(12) United States Patent
Perlstein et al.

(10) Patent No.: US 11,160,794 B2
(45) Date of Patent: Nov. 2, 2021

(54) METHODS FOR TREATING CONGENITAL DISORDERS OF GLYCOSYLATION

(71) Applicant: Maggie's Pearl, LLC, Sturgis, MI (US)

(72) Inventors: Ethan Oren Perlstein, Oakland, CA (US); Jessica Lao, Alameda, CA (US); Feba Sam, Sunnyvale, CA (US); Nina DiPrimio, San Francisco, CA (US); Zachary Parton, Oakland, CA (US); Hillary Tsang, San Francisco, CA (US); Kausalya Murthy, Mountain View, CA (US); Sangeetha Venkatraman Iyer, San Jose, CA (US); Joshua Mast, Hayward, CA (US); Tamy May Sharly Portillo Rodriguez, Antioch, CA (US); Madeleine Prangley, San Bruno, CA (US)

(73) Assignee: Maggie's Pearl, LLC, Sturgis, MI (US)

( * ) Notice: Subject to any disclaimer, the term of this patent is extended or adjusted under 35 U.S.C. 154(b) by 0 days.

(21) Appl. No.: 17/064,441

(22) Filed: Oct. 6, 2020

(65) Prior Publication Data

US 2021/0030721 A1 Feb. 4, 2021

Related U.S. Application Data

(63) Continuation of application No. PCT/US2019/030446, filed on May 2, 2019.

(60) Provisional application No. 62/760,311, filed on Nov. 13, 2018, provisional application No. 62/730,974, filed on Sep. 13, 2018, provisional application No. 62/765,356, filed on Aug. 20, 2018.

(51) Int. Cl.
*A61K 31/426* (2006.01)
*A61K 31/192* (2006.01)
*A61K 45/06* (2006.01)

(52) U.S. Cl.
CPC .......... *A61K 31/426* (2013.01); *A61K 31/192* (2013.01); *A61K 45/06* (2013.01)

(58) Field of Classification Search
None
See application file for complete search history.

(56) References Cited

FOREIGN PATENT DOCUMENTS

| EP | 1521761 | 1/2006 |
| EP | 3275863 | 1/2018 |
| WO | WO 2005/097773 | 10/2005 |
| WO | WO 2006/056604 | 6/2006 |

OTHER PUBLICATIONS

NORD, National Organization for Rare Disorders, "Congenital Disorders of Glycosylation", 2015, downloaded from "rarediseases.org/rare-diseases/congenital-disorders-of-glycosylation/", pp. 1-15 (Year: 2015).*
International Search Report & Written Opinion dated Aug. 15, 2019 for PCT/US2019/030446. 12 pages.
Citro, et al. The Analysis of Variants in the General Population Reveals That PMM2 Is Extremely Tolerant to Missense Mutations and That Diagnosis of PMM2-CDG Can Benefit from the Identification of Modifiers. Int J Mol Sci. Jul. 30, 2018;19(8):2218.
Sadowska-Nartosz, et al. Kinetics of glycoxidation of bovine serum albumin by glucose, fructose and ribose and its prevention by food components. Molecules. Nov. 17, 2014;19(11):18828-49.
Sangeetha Iyer, et al., "Repurposing the aldose reductase inhibitor and diabetic neuropathy drug epalrestat for the congenital disorder of glycosylation PMM2-CDG", (2019), The Company of Biologists Ltd, pp. 1-12, Disease Models & Mechanisms, vol. 12(11), Nov. 11, 2019.†

* cited by examiner
† cited by third party

*Primary Examiner* — Savitha M Rao
*Assistant Examiner* — Gregg Polansky
(74) *Attorney, Agent, or Firm* — Sheppard Mullin Richter & Hampton LLP

(57) ABSTRACT

The present disclosure relates generally to compounds and pharmaceutical compositions for increasing glycosylation and treating congenital disorders of glycosylation.

13 Claims, 11 Drawing Sheets

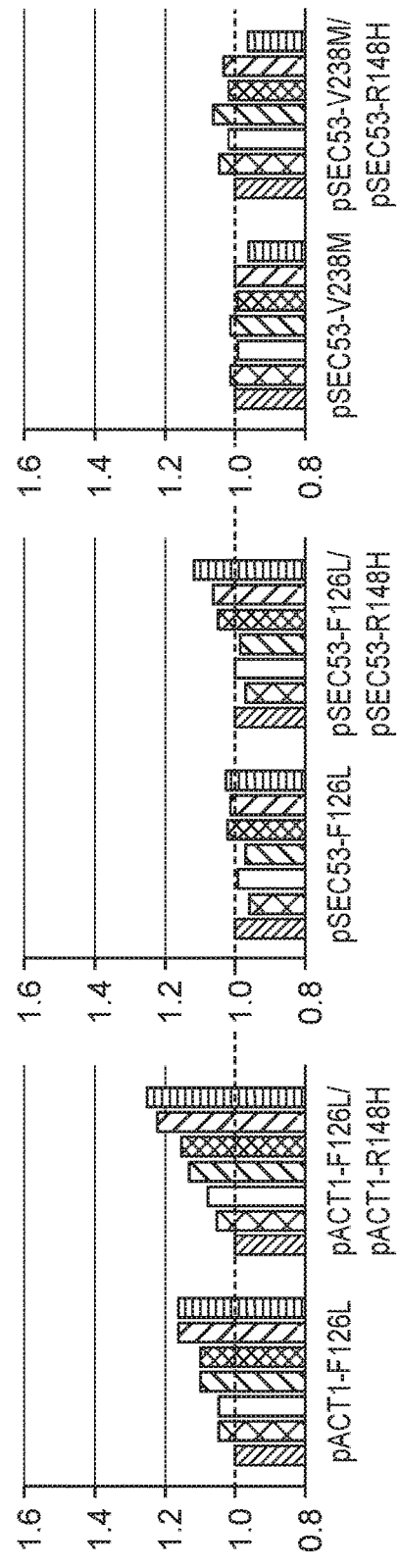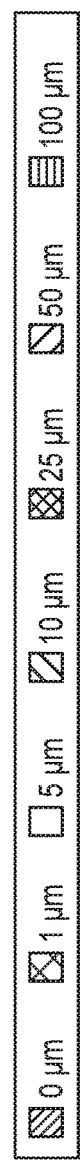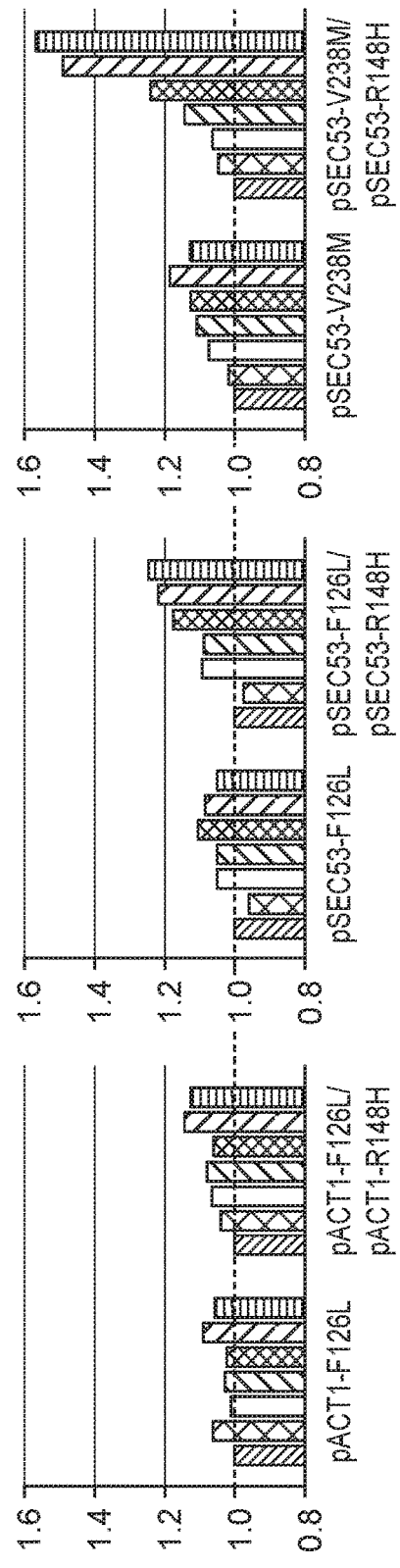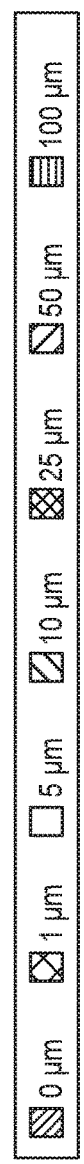
FIG. 1A
FIG. 1B

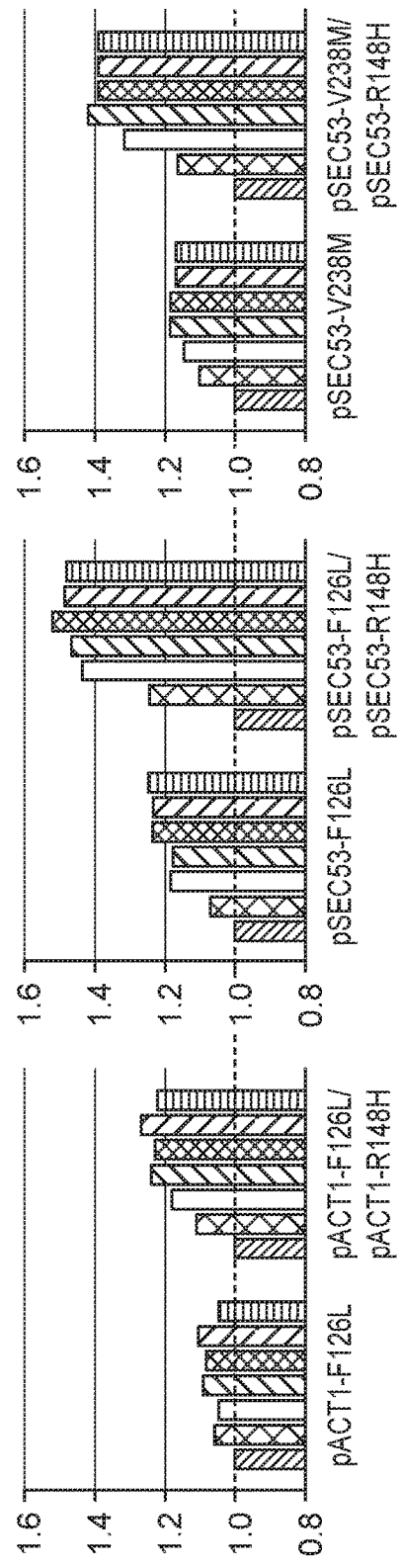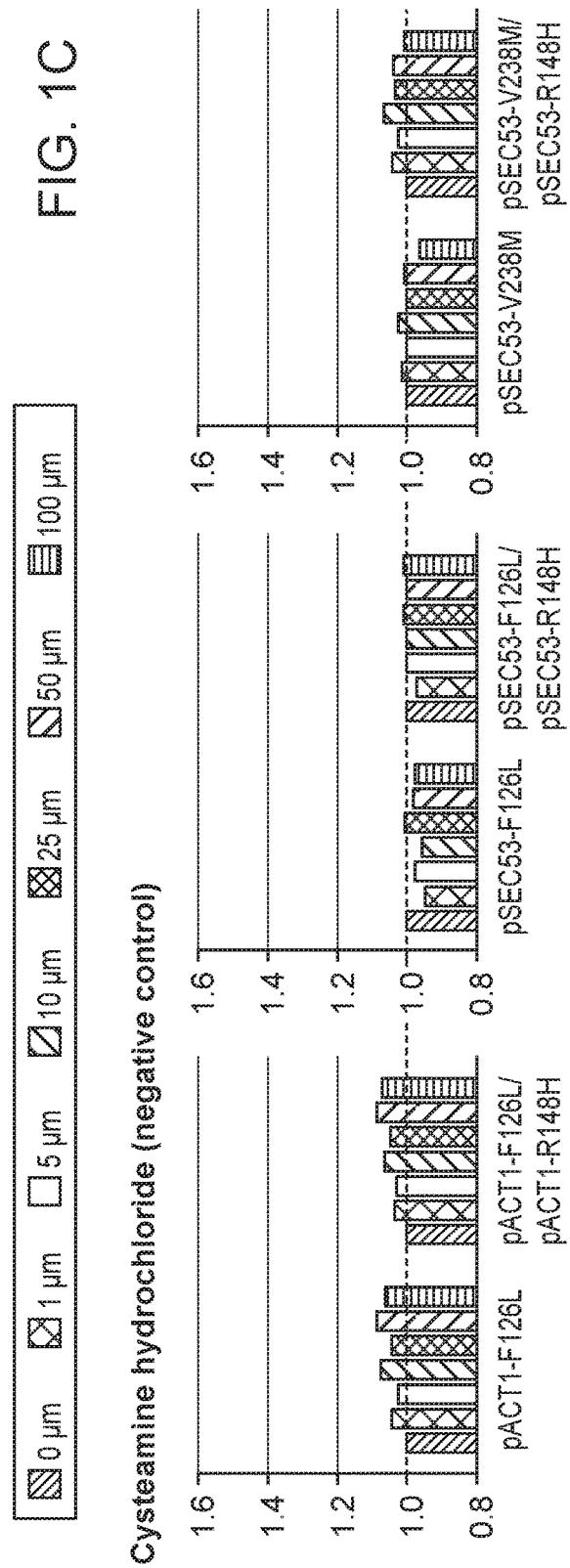
FIG. 1C
FIG. 1D

METHODS FOR TREATING CONGENITAL DISORDERS OF GLYCOSYLATION

CROSS-REFERENCE TO RELATED APPLICATIONS

This application is a continuation of International Application No. PCT/US2019/030446 filed May 2, 2019, which claims the benefit under 35 U.S.C. § 119(e) of U.S. Provisional Application 62/765,356, filed Aug. 20, 2018, U.S. Provisional Application 62/730,974, filed Sep. 13, 2018, and U.S. Provisional Application 62/760,311, filed Nov. 13, 2018, each of which is hereby incorporated by reference in its entirety.

FIELD

Provided herein compounds and pharmaceutical compositions for increasing glycosylation and treating congenital disorders of glycosylation.

BACKGROUND

Congenital disorders of glycosylation (CDG) include more than 130 inborn errors of metabolism that affects N-linked, O-linked protein and lipid-linked glycosylation. CDGs are typically classified as Types I (CDG-1) and II (CDG-II). Phosphomannomutase deficiency disease (PMM2 or PMM2-CDG) is the most common disorder of glycosylation with more than 800 patients reported worldwide.

PMM2 is a rare congenital disorder of glycosylation with no cure. It is an autosomal recessive disorder arising from a dysfunctional phosphomannomutase-2 gene. The phosphomannomutase-2 enzyme is responsible for transforming mannose 6-phosphate into mannose 1-phosphate, which in turn leads to the synthesis of GDP-mannose. Insufficient levels of GDP-mannose leads to under-glycosylated glycoproteins, lysosomal enzymes and serum proteins. This in turn is associated with increased proteasomal and oxidative stress. Thus, resolving the glycosylation defect, decreasing proteasomal stress, and decreasing oxidative stress may all or singly contribute to a therapeutic effect in the disease.

Clinical presentation of PMM2-CDG patients varies widely but almost all patients suffer from neuromuscular abnormalities, developmental delays, failure to thrive and multiple organ system involvement from liver to kidneys. Diagnosis occurs in early infancy due to repetitive medical problems associated with failure to thrive and grow according to normal milestones.

SUMMARY

The present disclosure provides methods for increasing glycosylation in a patient in need thereof comprising administering a therapeutically effective amount of a compound having the structure:

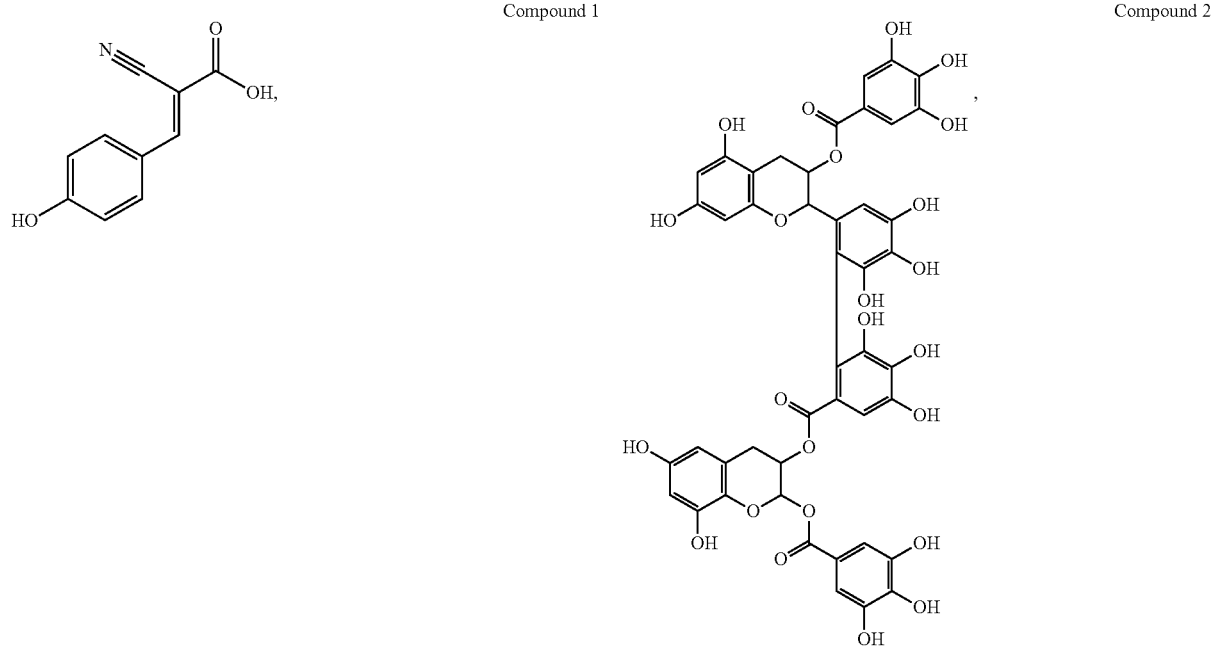

Compound 1

Compound 2

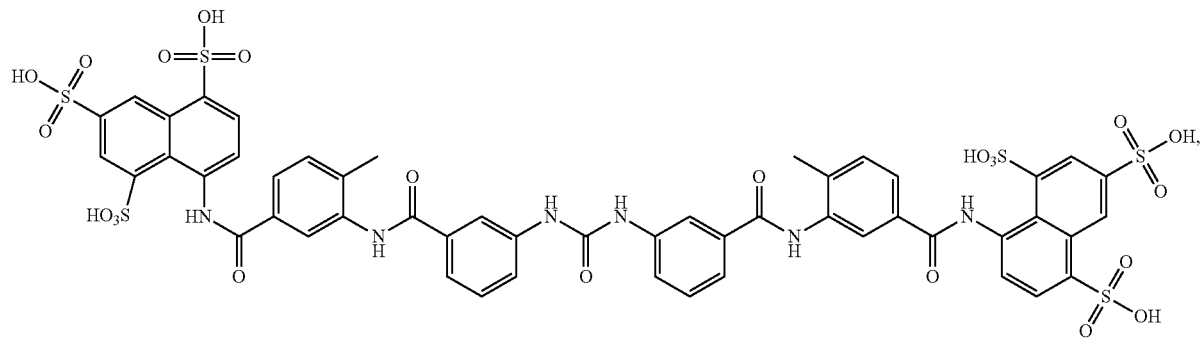

Compound 3 or a pharmaceutically acceptable salt thereof, or a combination thereof.

Also provided herein are methods for increasing glycosylation in a patient in need thereof comprising administering a therapeutically effective amount of an antioxidant.

Also provided herein are methods for increasing glycosylation in a patient in need thereof comprising administering a therapeutically effective amount of a compound selected from pyrogallin, amidol dihydrochloride, 3-methoxycatechol, hieracin, koparin, levodopa, and ethylnorepinephrine hydrochoride, or a pharmaceutically acceptable salt thereof.

Also provided herein are methods for increasing glycosylation in a patient in need thereof comprising administering a therapeutically effective amount of an aldose reductase inhibitor.

Also provided herein are methods for increasing glycosylation in a patient in need thereof comprising administering a pharmaceutical composition comprising a pharmaceutically acceptable carrier and a therapeutically effective amount of a compound having the structure:

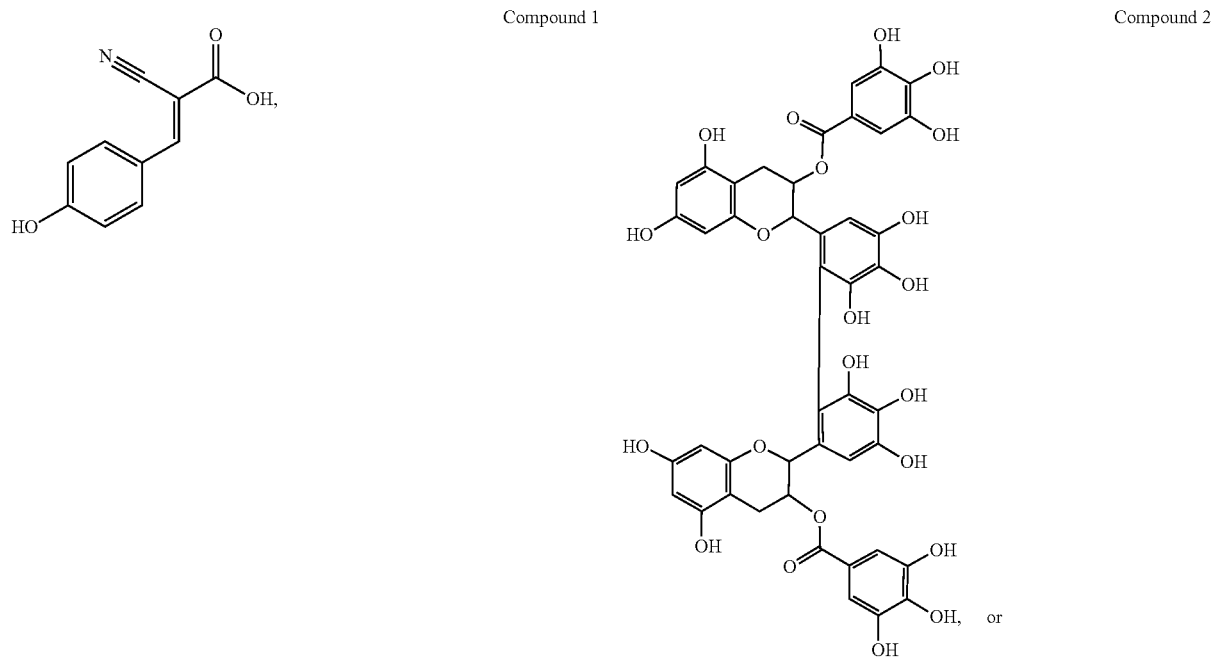

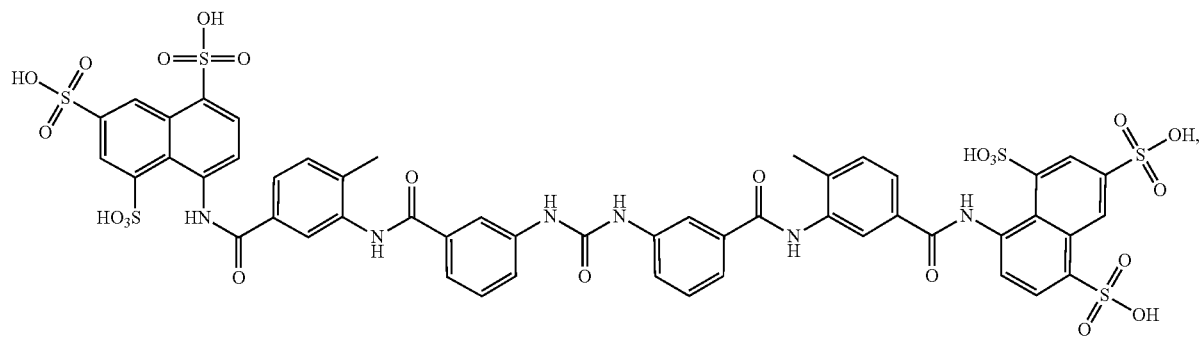
Compound 3 or a pharmaceutically acceptable salt thereof, or a combination thereof.

Also provided herein are methods for increasing glycosylation in a patient in need thereof comprising administering a pharmaceutical composition comprising a pharmaceutically acceptable carrier and a therapeutically effective amount of an antioxidant.

Also provided herein are methods for increasing glycosylation in a patient in need thereof comprising administering a pharmaceutical composition comprising a pharmaceutically acceptable carrier and a therapeutically effective amount of a compound selected from pyrogallin, amidol dihydrochloride, 3-methoxycatechol, hieracin, koparin, levodopa, and ethylnorepinephrine hydrochoride, or a pharmaceutically acceptable salt thereof.

Also provided herein are methods for increasing glycosylation in a patient in need thereof comprising administering a pharmaceutical composition comprising a pharmaceutically acceptable carrier and a therapeutically effective amount of an aldose reductase inhibitor.

Also provided herein are methods for treating a condition or disorder mediated, at least in part, by phosphomannomutase-2 enzyme in a patient in need thereof comprising administering a therapeutically effective amount of a compound having the structure:

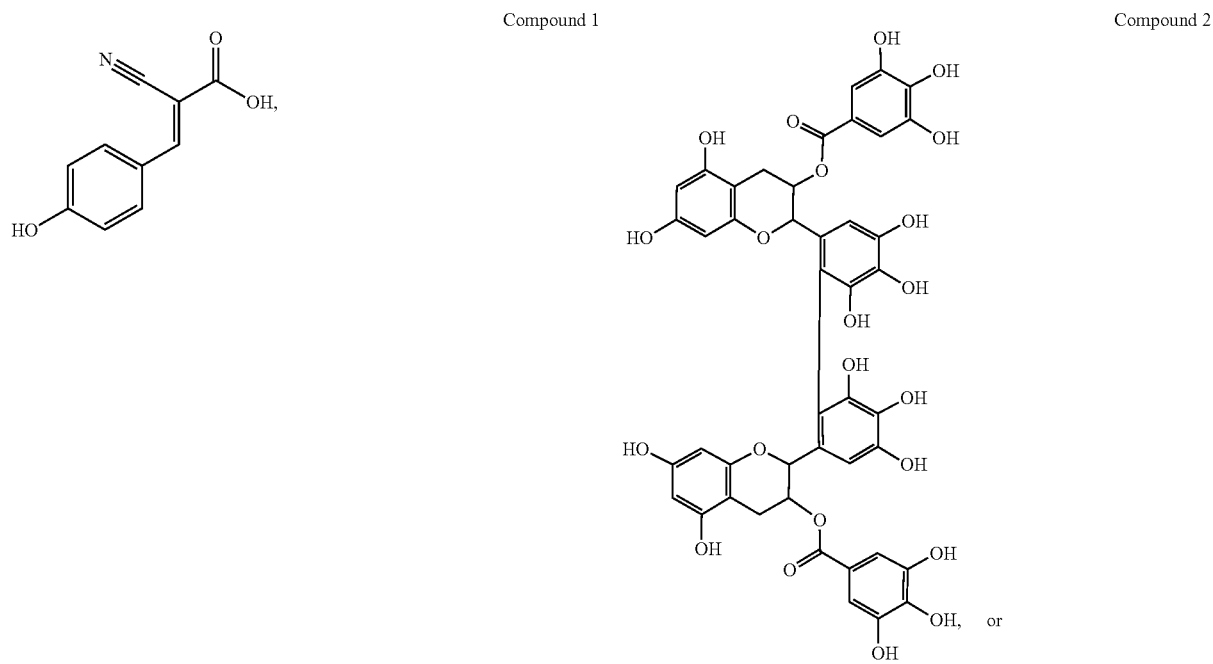

-continued

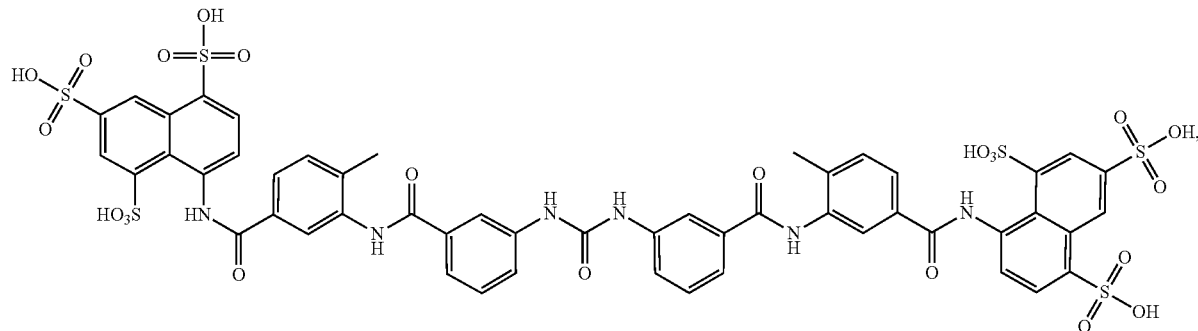

Compound 3 or a pharmaceutically acceptable salt thereof, or a combination thereof.

Also provided herein are methods for treating a condition or disorder mediated, at least in part, by phosphomannomutase-2 enzyme in a patient in need thereof comprising administering a therapeutically effective amount of an antioxidant.

Also provided herein are methods for treating a condition or disorder mediated, at least in part, by phosphomannomutase-2 enzyme in a patient in need thereof comprising administering a therapeutically effective amount of a of a compound selected from pyrogallin, amidol dihydrochloride, 3-methoxycatechol, hieracin, koparin, levodopa, and ethylnorepinephrine hydrochoride, or a pharmaceutically acceptable salt thereof.

Also provided herein are methods for treating a condition or disorder mediated, at least in part, by phosphomannomutase-2 enzyme in a patient in need thereof comprising administering a therapeutically effective amount of an aldose reductase inhibitor.

Also provided herein are methods for treating a condition or disorder mediated, at least in part, by phosphomannomutase-2 enzyme in a patient in need thereof comprising administering a pharmaceutical composition comprising a pharmaceutically acceptable carrier and a therapeutically effective amount of a compound having the structure:

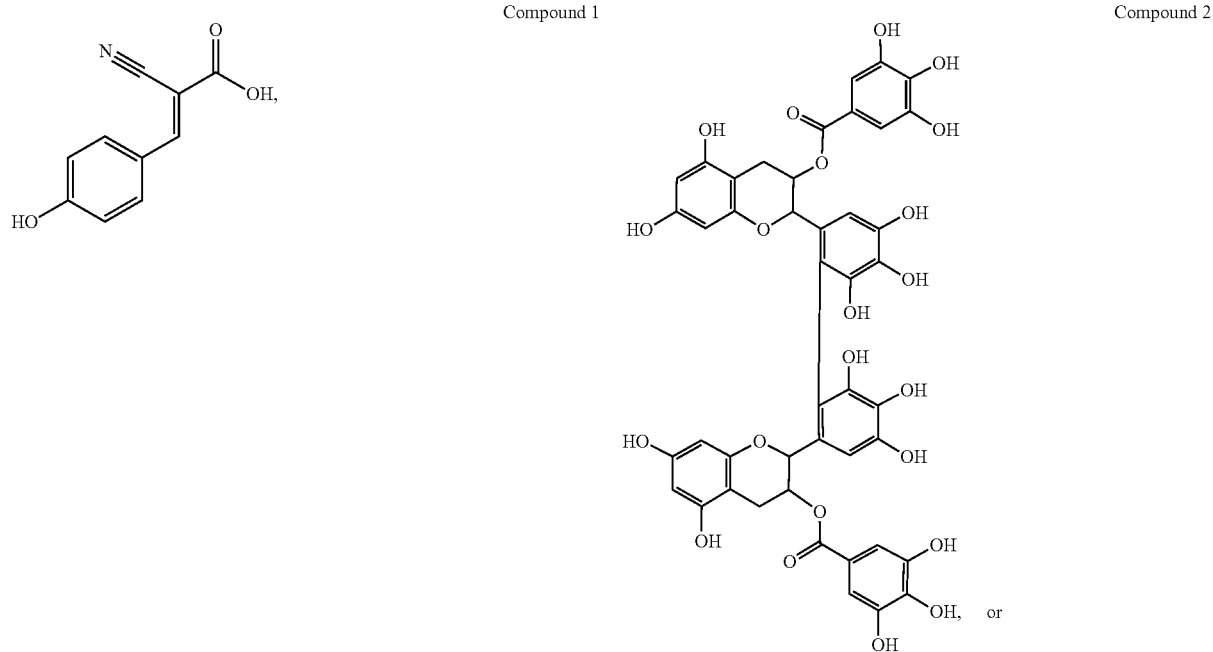

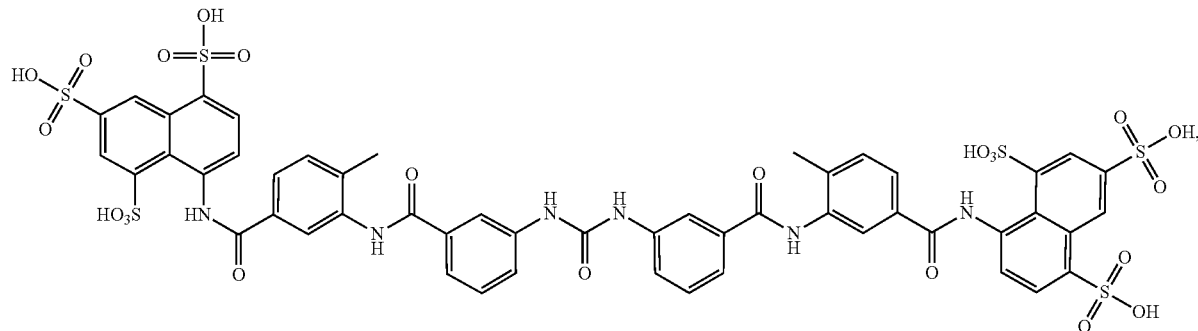

Compound 3 or a pharmaceutically acceptable salt thereof, or a combination thereof.

Also provided herein are methods for treating a condition or disorder mediated, at least in part, by phosphomannomutase-2 enzyme in a patient in need thereof comprising administering a pharmaceutical composition comprising a pharmaceutically acceptable carrier and a therapeutically effective amount of an antioxidant.

Also provided herein are methods for treating a condition or disorder mediated, at least in part, by phosphomannomutase-2 enzyme in a patient in need thereof comprising administering a pharmaceutical composition comprising a pharmaceutically acceptable carrier and a therapeutically effective amount of a compound selected from pyrogallin, amidol dihydrochloride, 3-methoxycatechol, hieracin, koparin, levodopa, and ethylnorepinephrine hydrochoride, or a pharmaceutically acceptable salt thereof.

Also provided herein are methods for treating a condition or disorder mediated, at least in part, by phosphomannomutase-2 enzyme in a patient in need thereof comprising administering a pharmaceutical composition comprising a pharmaceutically acceptable carrier and a therapeutically effective amount of an aldose reductase inhibitor.

Also provided herein are methods for treating a congenital disorder of glycosylation in a patient in need thereof comprising administering a therapeutically effective amount of a compound having the structure:

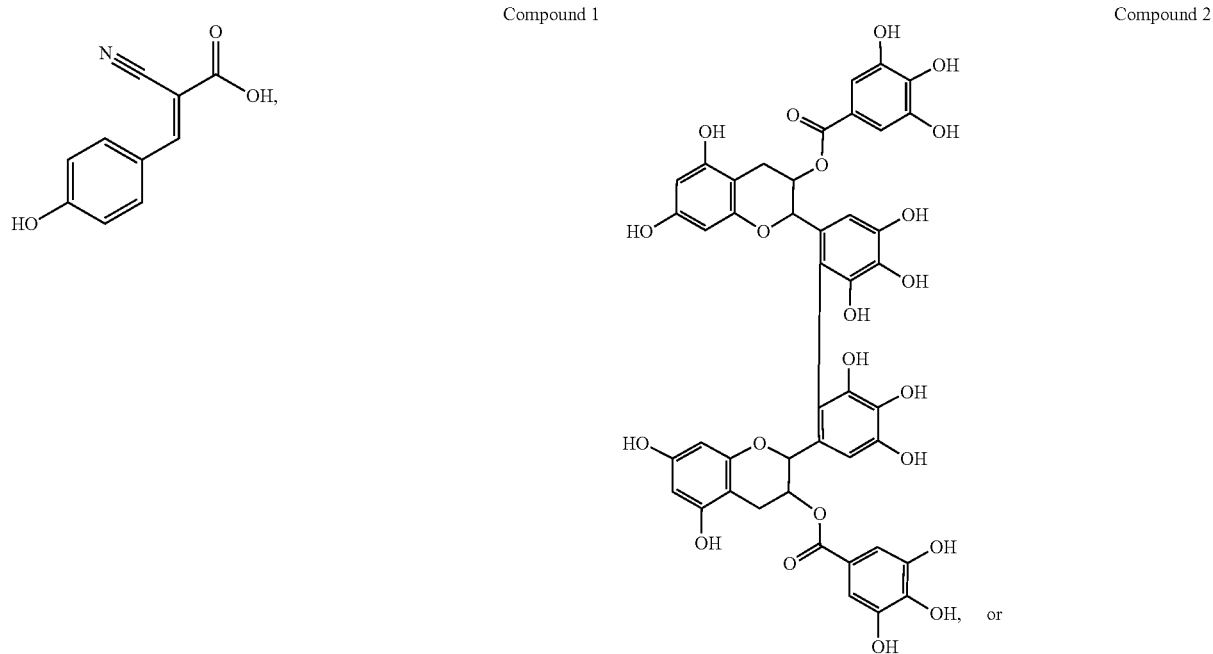

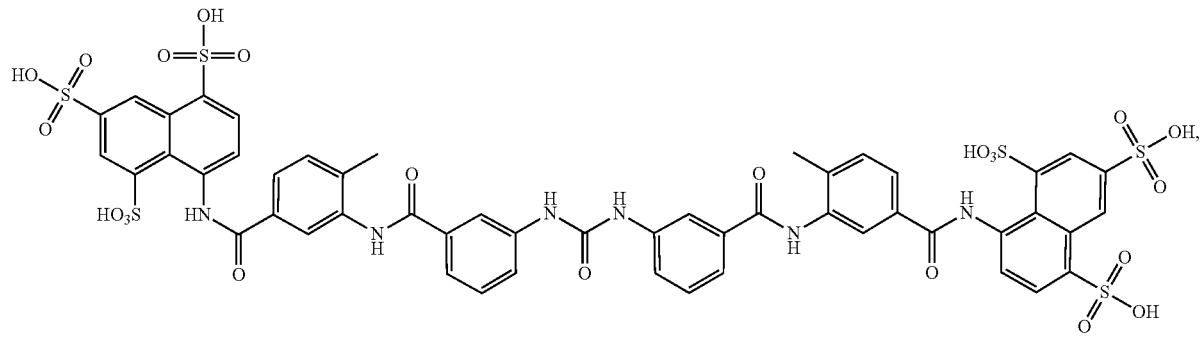

Compound 3 or a pharmaceutically acceptable salt thereof, or a combination thereof.

Also provided herein are methods for treating a congenital disorder of glycosylation in a patient in need thereof comprising administering a therapeutically effective amount of an antioxidant.

Also provided herein are methods for treating a congenital disorder of glycosylation in a patient in need thereof comprising administering a therapeutically effective amount of a compound selected from pyrogallin, amidol dihydrochloride, 3-methoxycatechol, hieracin, koparin, levodopa, and ethylnorepinephrine hydrochoride, or a pharmaceutically acceptable salt thereof.

Also provided herein are methods for treating a congenital disorder of glycosylation in a patient in need thereof comprising administering a therapeutically effective amount of an aldose reductase inhibitor.

Also provided herein are methods for treating a congenital disorder of glycosylation in a patient in need thereof comprising administering a pharmaceutical composition comprising a pharmaceutically acceptable carrier and a therapeutically effective amount of a compound having the structure:

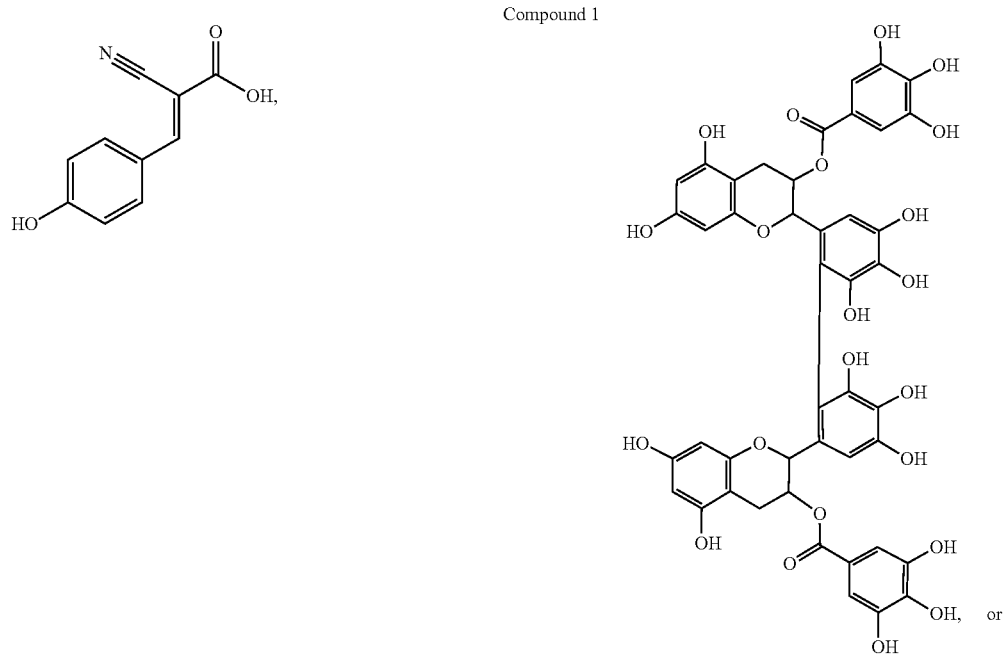

Compound 1

Compound 2

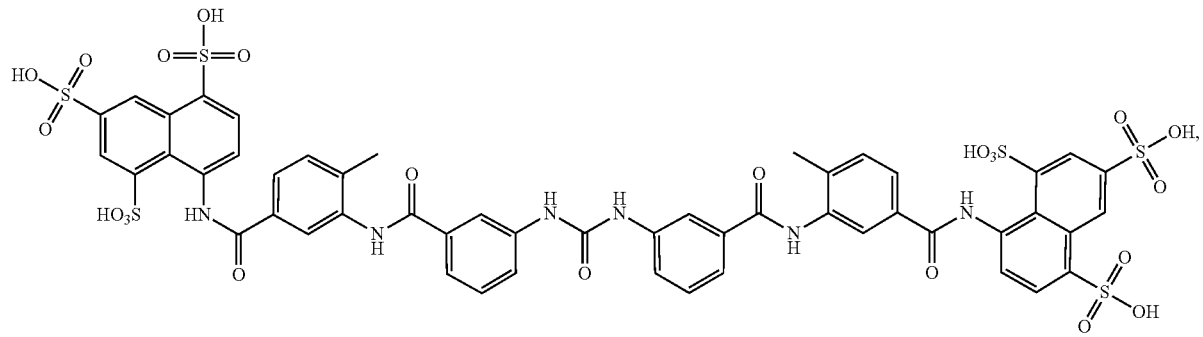
Compound 3 or a pharmaceutically acceptable salt thereof, or a combination thereof.

Also provided herein are methods for treating a congenital disorder of glycosylation in a patient in need thereof comprising administering a pharmaceutical composition comprising a pharmaceutically acceptable carrier and a therapeutically effective amount of an antioxidant.

Also provided herein are methods for treating a congenital disorder of glycosylation in a patient in need thereof comprising administering a pharmaceutical composition comprising a pharmaceutically acceptable carrier and a therapeutically effective amount of a compound selected from pyrogallin, amidol dihydrochloride, 3-methoxycatechol, hieracin, koparin, levodopa, and ethylnorepinephrine hydrochoride, or a pharmaceutically acceptable salt thereof.

Also provided herein are methods for treating a congenital disorder of glycosylation in a patient in need thereof comprising administering a pharmaceutical composition comprising a pharmaceutically acceptable carrier and a therapeutically effective amount of an aldose reductase inhibitor.

Also provided herein are methods for treating phosphomannomutase deficiency in a patient in need thereof comprising administering a therapeutically effective amount of a compound having the structure:

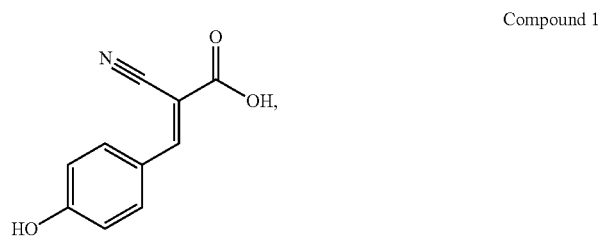
Compound 1

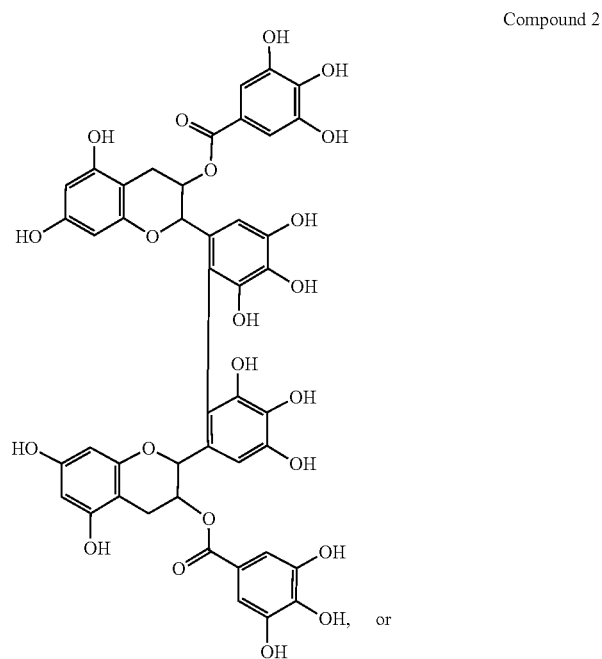
Compound 2 or

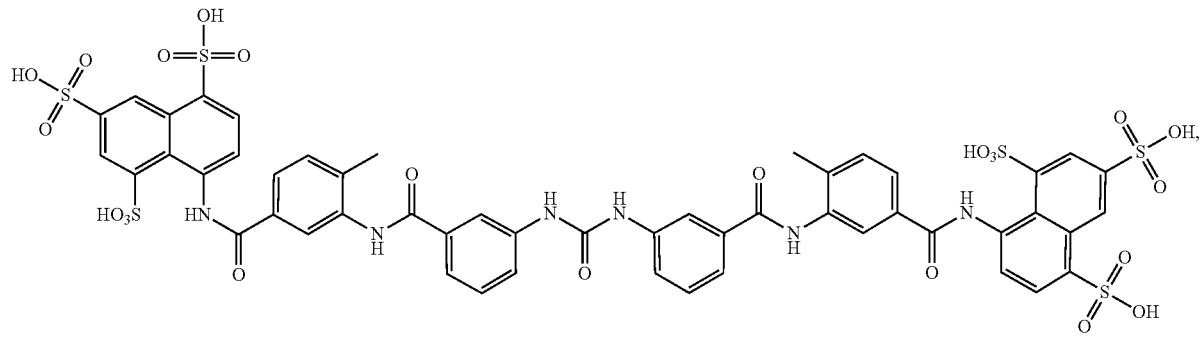

Compound 3 or a pharmaceutically acceptable salt thereof, or a combination thereof.

Also provided herein are methods for treating phosphomannomutase deficiency in a patient in need thereof comprising administering a therapeutically effective amount of an antioxidant.

Also provided herein are methods for treating phosphomannomutase deficiency in a patient in need thereof comprising administering a therapeutically effective amount of a compound selected from pyrogallin, amidol dihydrochloride, 3-methoxycatechol, hieracin, koparin, levodopa, and ethylnorepinephrine hydrochoride, or a pharmaceutically acceptable salt thereof.

Also provided herein are methods for treating phosphomannomutase deficiency in a patient in need thereof comprising administering a therapeutically effective amount of an aldose reductase inhibitor.

Also provided herein are methods for treating phosphomannomutase deficiency in a patient in need thereof comprising administering a pharmaceutical composition comprising a pharmaceutically acceptable carrier and a therapeutically effective amount of a compound having the structure:

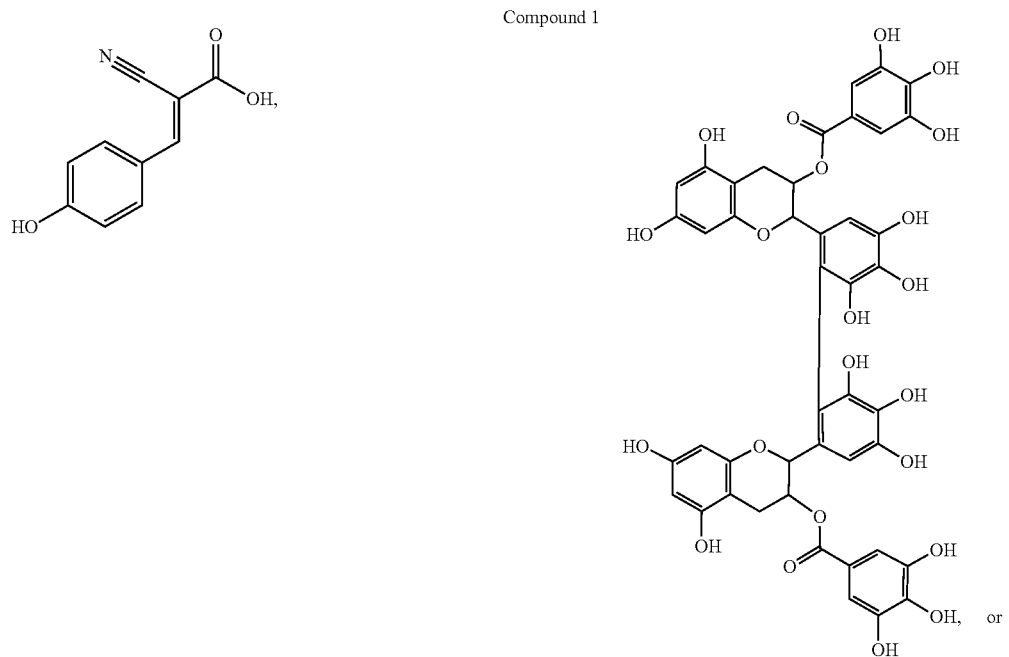

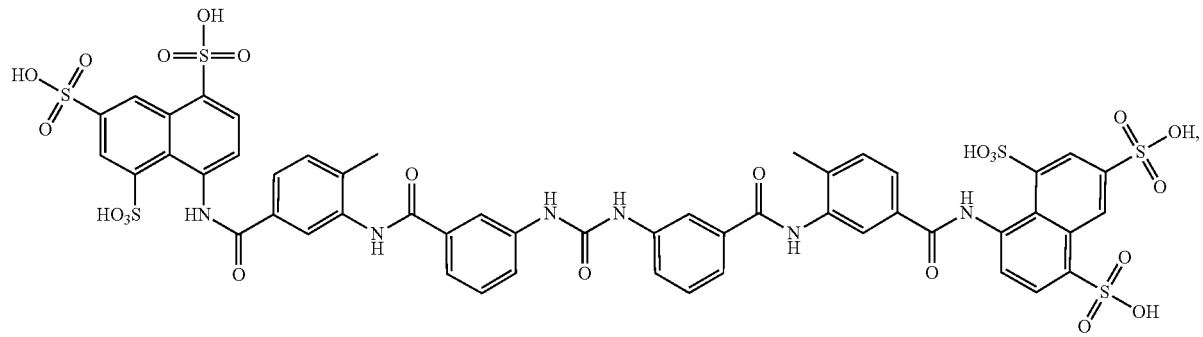

Compound 3 or a pharmaceutically acceptable salt thereof, or a combination thereof.

Also provided herein are methods for treating phosphomannomutase deficiency in a patient in need thereof comprising administering a pharmaceutical composition comprising a pharmaceutically acceptable carrier and a therapeutically effective amount of an antioxidant.

Also provided herein are methods for treating phosphomannomutase deficiency in a patient in need thereof comprising administering a pharmaceutical composition comprising a pharmaceutically acceptable carrier and a therapeutically effective amount of a compound selected from pyrogallin, amidol dihydrochloride, 3-methoxycatechol, hieracin, koparin, levodopa, and ethylnorepinephrine hydrochoride, or a pharmaceutically acceptable salt thereof.

Also provided herein are methods for treating phosphomannomutase deficiency in a patient in need thereof comprising administering a pharmaceutical composition comprising a pharmaceutically acceptable carrier and a therapeutically effective amount of an aldose reductase inhibitor.

BRIEF DESCRIPTION OF THE DRAWINGS

The compounds described herein show differential reuse of growth of SEC53 alleles. Specifically, α-cyano-4-hydroxycinnamic acid ("Compound 1," FIG. 1A), 2',2'-bisepigallocatechin digallate ("Compound 2," FIG. 1B), and suramin hexasodium (a hexasodium salt of "Compound 3," FIG. 1C) showed consistent and dose-dependent rescues in haploid and heterozygous diploid cells while the negative control compound, cysteamine hydrochloride, does not rescue at any dose (FIG. 1D). These data are normalized to the first time point.

α-cyano-4-hydroxycinnamic acid ("Compound 1," FIG. 2A), 2',2'-bisepigallocatechin digallate ("Compound 2," FIG. 2B), and suramin hexasodium (a hexasodium salt of "Compound 3," FIG. 2C) showed consistent and dose-dependent rescues in haploid and heterozygous diploid cells while the negative control compound, cysteamine hydrochloride, does not rescue at any dose (FIG. 2D). Mean and standard error shown from 16 samples. These data are not normalized and show absolute growth of pmm2 mutant yeast in response to different drugs.

DETAILED DESCRIPTION

Definitions

Figure 2A:
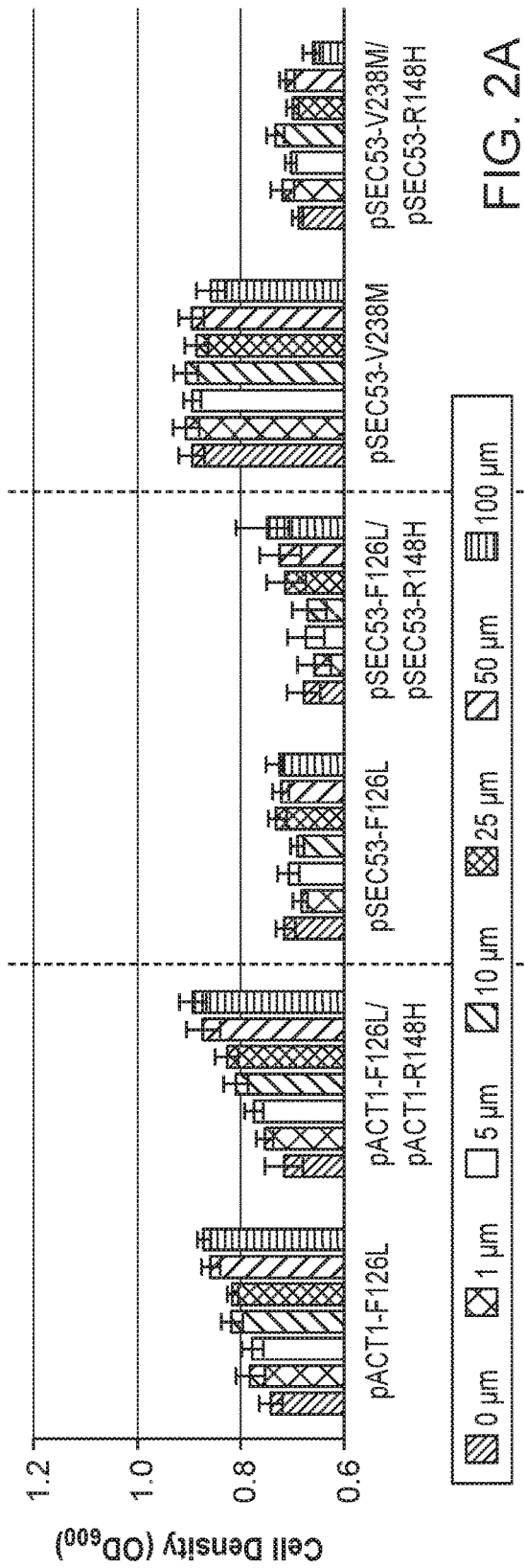

The following description sets forth exemplary embodiments of the present technology. It should be recognized, however, that such description is not intended as a limitation on the scope of the present disclosure but is instead provided as a description of exemplary embodiments.

As used in the present specification, the following words, phrases and symbols are generally intended to have the meanings as set forth below, except to the extent that the context in which they are used indicates otherwise.

Reference to "about" a value or parameter herein includes (and describes) embodiments that are directed to that value or parameter per se. In certain embodiments, the term "about" includes the indicated amount ±10%. In other embodiments, the term "about" includes the indicated amount ±5%. In certain other embodiments, the term "about" includes the indicated amount ±1%. In certain other embodiments, the term "about" includes the indicated amount ±0.05%. Also, to the term "about X" includes description of "X."

Also, the singular forms "a" and "the" include plural references unless the context clearly dictates otherwise. Thus, e.g., reference to "the compound" includes a plurality of such compounds and reference to "the assay" includes reference to one or more assays and equivalents thereof known to those skilled in the art.

Provided are also pharmaceutically acceptable salts, stereoisomers, mixture of stereoisomers, hydrates, solvates, solid forms, and tautomeric forms of the compounds described herein.

In many cases, the compounds of this disclosure are capable of forming acid and/or base salts by virtue of the presence of amino and/or carboxyl groups or groups similar thereto.

"Pharmaceutically acceptable" or "physiologically acceptable" refer to compounds, salts, compositions, dosage forms and other materials which are useful in preparing a pharmaceutical composition that is suitable for veterinary or human pharmaceutical use.

The term "pharmaceutically acceptable salt" of a given compound refers to salts that retain the biological effectiveness and properties of the given compound, and which are not biologically or otherwise undesirable. "Pharmaceutically acceptable salts" or "physiologically acceptable salts" include, for example, salts with inorganic acids and salts with an organic acid. In addition, if the compounds described herein are obtained as an acid addition salt, the free base can be obtained by basifying a solution of the acid salt. Conversely, if the product is a free base, an addition salt, particularly a pharmaceutically acceptable addition salt, may be produced by dissolving the free base in a suitable organic solvent and treating the solution with an acid, in accordance with conventional procedures for preparing acid addition salts from base compounds. Those skilled in the art will recognize various synthetic methodologies that may be used to prepare nontoxic pharmaceutically acceptable addition salts. Pharmaceutically acceptable acid addition salts may be prepared from inorganic and organic acids. Salts derived from inorganic acids include hydrochloric acid, hydrobromic acid, sulfuric acid, nitric acid, phosphoric acid, and the like. Salts derived from organic acids include acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluene-sulfonic acid, salicylic acid, and the like. Likewise, pharmaceutically acceptable base addition salts can be prepared from inorganic and organic bases. Salts derived from inorganic bases include, by way of example only, sodium, potassium, lithium, ammonium, calcium and magnesium salts. Salts derived from organic bases include, but are not limited to, salts of primary, secondary and tertiary amines. Specific examples of suitable amines include, by way of example only, isopropylamine, trimethyl amine, diethyl amine, tri(iso-propyl) amine, tri(n-propyl) amine, ethanolamine, 2-dimethylaminoethanol, piperazine, piperidine, morpholine, N-ethylpiperidine, and the like.

The term "solvate" refers to a complex formed by a combination of solvent molecules with molecules or ions of the solute. The solvent can be an organic compound, an inorganic compound, or a mixture of both. As used herein, the term "solvate" includes a "hydrate" (i.e., a complex formed by combination of water molecules with molecules or ions of the solute), hemi-hydrate, channel hydrate, etc. Some examples of solvents include, but are not limited to, methanol, N,N-dimethylformamide, tetrahydrofuran, dimethylsulfoxide, and water. In general, the solvated forms are equivalent to unsolvated forms and are encompassed within the scope of the present disclosure.

The term "solid form" refers to a type of solid-state material that includes amorphous as well as crystalline forms. The term "crystalline form" refers to polymorphs as well as solvates, hydrates, etc. The term "polymorph" refers to a particular crystal structure having particular physical properties such as X-ray diffraction, melting point, and the like.

Some of the compounds exist as tautomers. Tautomers are in equilibrium with one another. For example, amide containing compounds may exist in equilibrium with imidic acid tautomers. Regardless of which tautomer is shown, and regardless of the nature of the equilibrium among tautomers, the compounds are understood by one of ordinary skill in the art to comprise both amide and imidic acid tautomers. Thus, the amide containing compounds are understood to include their imidic acid tautomers. Likewise, the imidic acid containing compounds are understood to include their amide tautomers.

Any formula or structure given herein, is also intended to represent unlabeled forms as well as isotopically labeled forms of the compounds. Isotopically labeled compounds have structures depicted by the formulas given herein except that one or more atoms are replaced by an atom having a selected atomic mass or mass number. Examples of isotopes that can be incorporated into compounds of the disclosure include isotopes of hydrogen, carbon, nitrogen, oxygen, phosphorous, fluorine and chlorine, such as, but not limited to $^2$H (deuterium, D), $^3$H (tritium), $^{11}$C, $^{13}$C, $^{14}$C, $^{15}$N, $^{18}$F, $^{31}$P, $^{32}$P, $^{35}$S, $^{36}$Cl and $^{125}$I. Various isotopically labeled compounds of the present disclosure include, for example, those into which radioactive isotopes such as $^3$H, $^{13}$C and $^{14}$C are incorporated. Such isotopically labelled compounds may be useful in metabolic studies, reaction kinetic studies, detection or imaging techniques, such as positron emission tomography (PET) or single-photon emission computed tomography (SPECT) including drug or substrate tissue distribution assays or in radioactive treatment of patients.

The disclosure also includes "deuterated analogs" of compounds described herein in which from 1 to n hydrogens attached to a carbon atom is/are replaced by deuterium, in which n is the number of hydrogens in the molecule. Such compounds exhibit increased resistance to metabolism and are thus useful for increasing the half-life of any compound described herein when administered to a mammal, particularly a human. See, for example, Foster, "Deuterium Isotope Effects in Studies of Drug Metabolism," Trends Pharmacol. Sci. 5(12):524-527 (1984). Such compounds are synthesized by means well known in the art, for example by employing starting materials in which one or more hydrogens have been replaced by deuterium.

Deuterium labelled or substituted therapeutic compounds of the disclosure may have improved DMPK (drug metabolism and pharmacokinetics) properties, relating to distribution, metabolism and excretion (ADME). Substitution with heavier isotopes such as deuterium may afford certain therapeutic advantages resulting from greater metabolic stability, for example increased in vivo half-life, reduced dosage requirements and/or an improvement in therapeutic index. An $^{18}$F labeled compound may be useful for PET or SPECT studies. Isotopically labeled compounds of this disclosure can generally be prepared by carrying out syntheses known in the art and substituting a readily available isotopically labeled reagent for a non-isotopically labeled reagent.

The concentration of such a heavier isotope, specifically deuterium, may be defined by an isotopic enrichment factor In the compounds of this disclosure any atom not specifically designated as a particular isotope is meant to represent any stable isotope of that atom. Unless otherwise stated, when a position is designated specifically as "H" or "hydrogen", the position is understood to have hydrogen at its natural abundance isotopic composition. Accordingly, in the compounds of this disclosure any atom specifically designated as a deuterium (D) is meant to represent deuterium.

As used herein, "pharmaceutically acceptable carrier" or "pharmaceutically acceptable excipient" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the active ingredient, its use in the therapeutic compositions is contemplated. Supplementary active ingredients can also be incorporated into the compositions.

"Treatment" or "treating" is an approach for obtaining beneficial or desired results including clinical results. Beneficial or desired clinical results may include one or more of the following: a) inhibiting the disease or condition (e.g., decreasing one or more symptoms resulting from the disease or condition, and/or diminishing the extent of the disease or condition); b) slowing or arresting the development of one or more clinical symptoms associated with the disease or condition (e.g., stabilizing the disease or condition, preventing or delaying the worsening or progression of the disease or condition, and/or preventing or delaying the spread (e.g., metastasis) of the disease or condition); and/or c) relieving the disease, that is, causing the regression of clinical symptoms (e.g., ameliorating the disease state, providing partial or total remission of the disease or condition, enhancing effect of another medication, delaying the progression of the disease, increasing the quality of life, and/or prolonging survival.

"Prevention" or "preventing" means any treatment of a disease or condition that causes the clinical symptoms of the disease or condition not to develop. Compounds may, in some embodiments, be administered to a subject (including a human) who is at risk or has a family history of the disease or condition.

"Subject" or "patient" refers to an animal, such as a mammal (including a human), that has been or will be the object of treatment, observation or experiment. The methods described herein may be useful in human therapy and/or veterinary applications. In some embodiments, the subject or patient is a mammal. In some embodiments, the subject or patient is a human.

The term "therapeutically effective amount" or "effective amount" of a compound described herein means an amount sufficient to effect treatment when administered to a subject, to provide a therapeutic benefit such as amelioration of symptoms or slowing of disease progression. For example, a therapeutically effective amount may be an amount sufficient to decrease a symptom of a condition or disorder described herein, including but not limited to phosphomannomutase deficiency. The therapeutically effective amount may vary depending on the subject, and disease or condition being treated, the weight and age of the subject, the severity of the disease or condition, and the manner of administering, which can readily be determined by one or ordinary skill in the art.

The methods described herein may be applied to cell populations in vivo or ex vivo. "In vivo" means within a living individual, as within an animal or human. In this context, the methods described herein may be used therapeutically in an individual. "Ex vivo" means outside of a living individual. Examples of ex vivo cell populations include in vitro cell cultures and biological samples including fluid or tissue samples obtained from individuals. Such samples may be obtained by methods well known in the art. Exemplary biological fluid samples include blood, cerebrospinal fluid, urine, and saliva. In this context, the compounds and compositions described herein may be used for a variety of purposes, including therapeutic and experimental purposes. For example, the compounds and compositions described herein may be used ex vivo to determine the optimal schedule and/or dosing of administration of a compound of the present disclosure for a given indication, cell type, individual, and other parameters. Information gleaned from such use may be used for experimental purposes or in the clinic to set protocols for in vivo treatment. Other ex vivo uses for which the compounds and compositions described herein may be suited are described below or will become apparent to those skilled in the art. The selected compounds may be further characterized to examine the safety or tolerance dosage in human or non-human subjects. Such properties may be examined using commonly known methods to those skilled in the art.

Compounds, Pharmaceutical Compositions, and Modes of Administration

Provided herein are compounds useful for increasing glycosylation and/or treating a congenital disorder of glycosylation.

In some embodiments, the compound has the following structure:

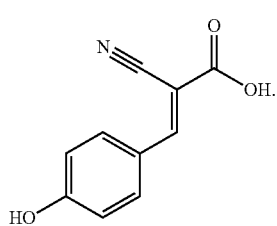

Compound 1

In some embodiments, the compound is a pharmaceutically acceptable salt of Compound 1. Compound 1, also known as α-cyano-4-hydroxycinnamic acid, is commercially available and also may be synthesized according to methods known in the art. Compound 1 is also known as an aldose reductase inhibitor.

In some embodiments, the compound has the following structure:

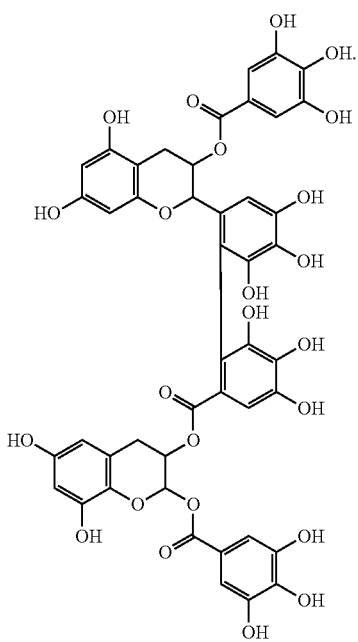 [SMILES: O=C(OC1Cc2c(O)cc(O)cc2OC1c1cc(O)c(O)c(O)c1-c1c(C(=O)OC2Cc3cc(O)cc(O)c3OC2OC(=O)c2cc(O)c(O)c(O)c2)cc(O)c(O)c1O)c1cc(O)c(O)c(O)c1]

In some embodiments, the compound is a pharmaceutically acceptable salt of Compound 2. Compound 2, also known as [2-[2-[6-[5,7-dihydroxy-3-(3,4,5-trihydroxybenzoyl)oxy-3,4-dihydro-2H-chromen-2-yl]-2,3,4-trihydroxyphenyl]-3,4,5-trihydroxyphenyl]-5,7-dihydroxy-3,4-dihydro-2H-chromen-3-yl]3,4,5-trihydroxybenzoate or 2',2'-bise- pigallocatechin digallate or theasinensin, is commercially available and also may be synthesized according to methods known in the art. Compound 2 is an active compound in oolong tea and is known to exhibit numerous antioxidant properties shared by other plant-based polyphenols.

In some embodiments, the compound is:

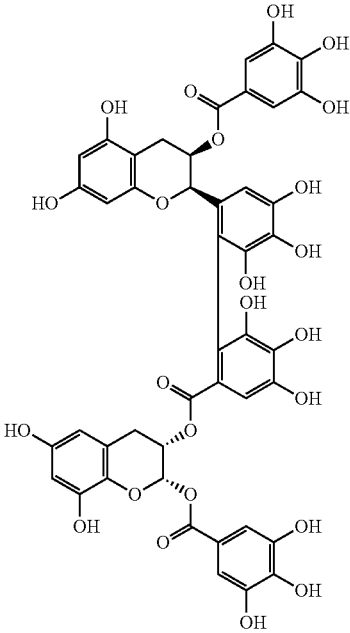 [SMILES: O=C(O[C@@H]1Oc2c(O)cc(O)cc2C[C@@H]1OC(=O)c1cc(O)c(O)c(O)c1-c1c([C@H]2Oc3cc(O)cc(O)c3C[C@H]2OC(=O)c2cc(O)c(O)c(O)c2)cc(O)c(O)c1O)c1cc(O)c(O)c(O)c1]

or a pharmaceutically acceptable salt.

In some embodiments, the compound is:

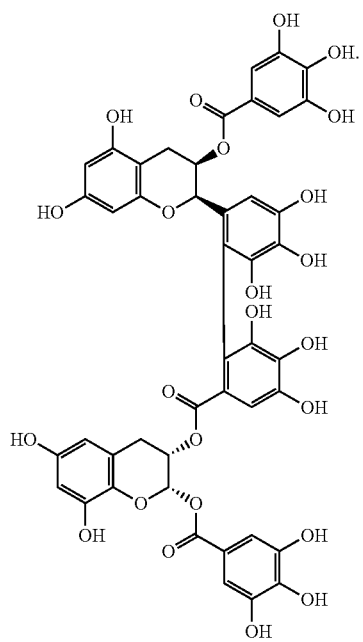

In some embodiments, the compound has the following structure:

Compound 3

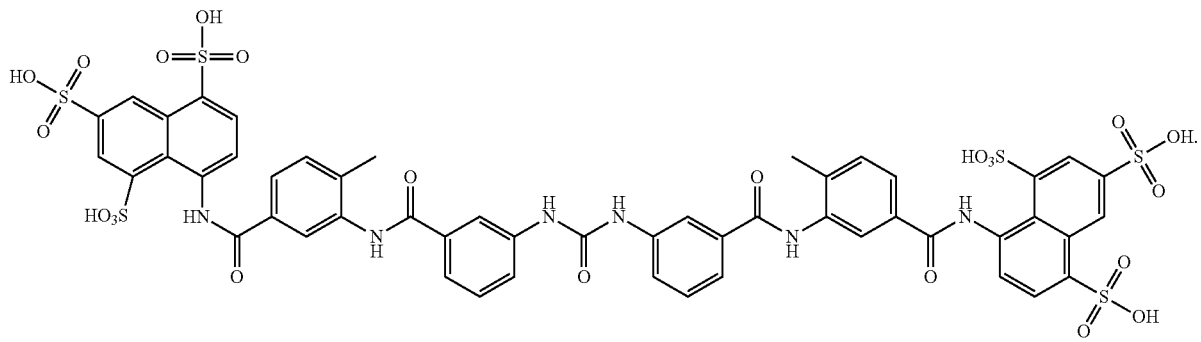

In some embodiments, the compound is a pharmaceutically acceptable salt of Compound 3. In some embodiments, the compound is a sodium salt of Compound 3. In some embodiments, the compound is a hexasodium salt of Compound 3.

Compound 3, also known as 8-[[4-methyl-3-[[3-[[3-[[2-methyl-5-[(4,6,8-trisulfonaphthalen-1-yl)carbamoyl]phenyl]carbamoyl]phenyl]carbamoylamino]benzoyl]amino]benzoyl]amino]naphth alene-1,3,5-trisulfonic acid or suramin, is commercially available and also may be synthesized according to methods known in the art.

In some embodiments, the compound is an antioxidant. An antioxidant is a compound that exhibits antioxidant properties; such compounds are capable of either delaying or inhibiting oxidation processes which can occur under the influence of atmospheric oxygen or reactive oxygen species. Methods of identifying whether a compound exhibits antioxidant properties are known. See Pisoschi and Negulescu, Biochem & Anal Biochem 2011, 1:106; Singh & Singh, Food Reviews International 2008, 24:4, 392-415, each of which are hereby incorporated by reference in their entirety.

In some embodiments, an antioxidant is Compound 2 or a pharmaceutically acceptable salt thereof.

In some embodiments, an antioxidant is a compound selected from the group consisting of:

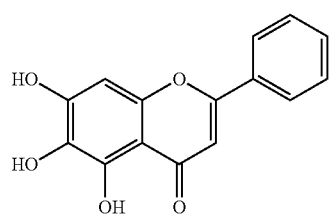 [SMILES: O=c1cc(-c2ccccc2)oc2cc(O)c(O)c(O)c12]

(also known as baicalein),

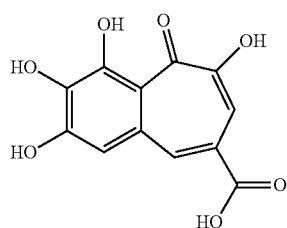 [SMILES: O=C(O)c1cc(O)c(=O)c2c(O)c(O)c(O)cc2c1]

(also known as purpurogallin-4-carboxylic acid),

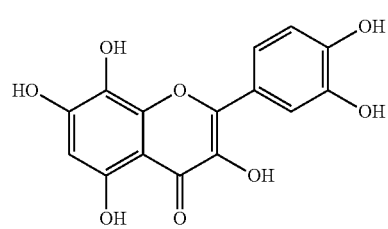 [SMILES: O=c1c(O)c(-c2ccc(O)c(O)c2)oc2c(O)c(O)cc(O)c12]

(also known as gossypetin),

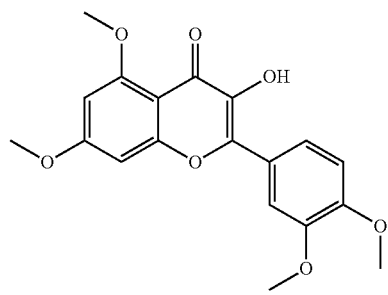

(also known as quercetin 5,7,3',4'-tetramethyl ether),

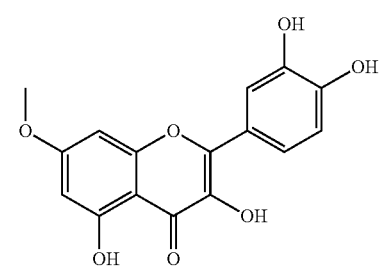 [SMILES: COc1cc(O)c2c(=O)c(O)c(-c3ccc(O)c(O)c3)oc2c1]

(also known as rhamnetin),

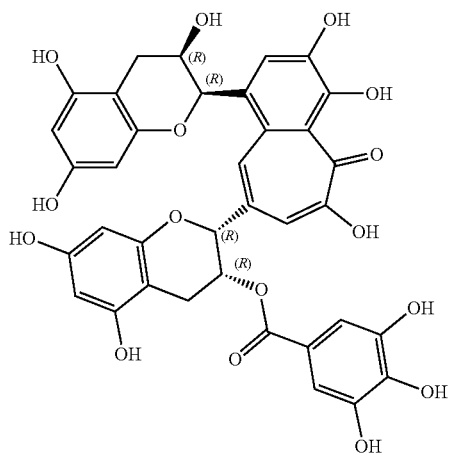

(also known as theaflavin monogallate),

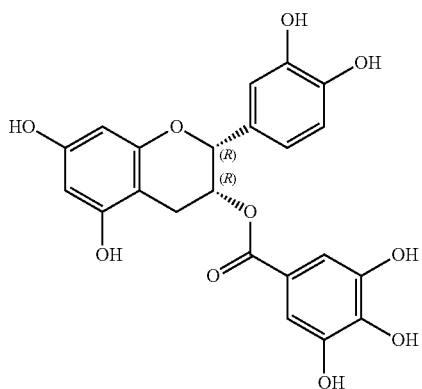

(also known as epicatechin monogallate),

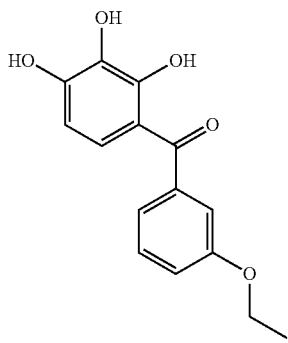 [SMILES: CCOc1cccc(C(=O)c2ccc(O)c(O)c2O)c1]

(also known as 3,4-didesmethyl-5-deshydroxy-3'-ethoxy-scleroin),

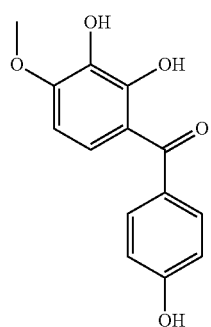 [SMILES: COc1ccc(C(=O)c2ccc(O)cc2)c(O)c1O]

(also known as 2,3,4'-trihydroxy-4-methoxybenzophenone),

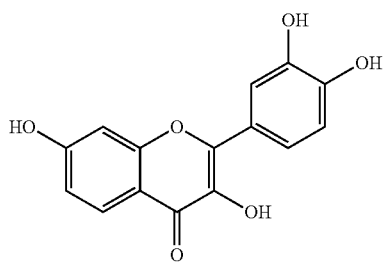 [SMILES: O=c1c(O)c(-c2ccc(O)c(O)c2)oc2cc(O)ccc12]

(also known as fisetin),

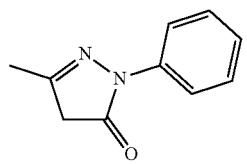

(also known as edaravone),

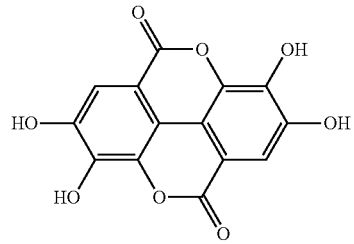 [SMILES: O=c1oc2c(O)c(O)cc3c(=O)oc4c(O)c(O)cc1c4c23]

(also known as ellagic acid), and

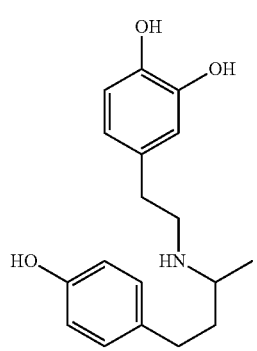 [SMILES: CC(CCc1ccc(O)cc1)NCCc1ccc(O)c(O)c1]

(also known as dobutamine hydrochloride),
or a pharmaceutically acceptable salt thereof. Such compounds are commercially available and also may be synthesized according to methods known in the art.

In some embodiments, the compound is selected from:

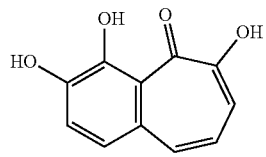 [SMILES: O=c1c(O)cccc2ccc(O)c(O)c12]

(also known as pyrogallin),

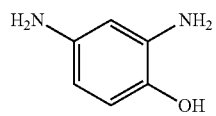

(also known as amidol dihydrochloride),

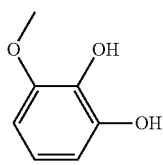

(also known as 3-methoxycatechol),

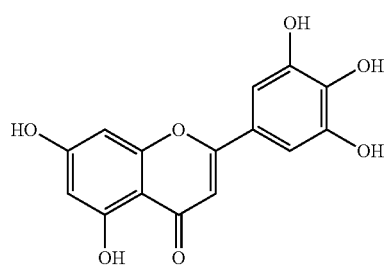 [SMILES: O=c1cc(-c2cc(O)c(O)c(O)c2)oc2cc(O)cc(O)c12]

(also known as hieracin),

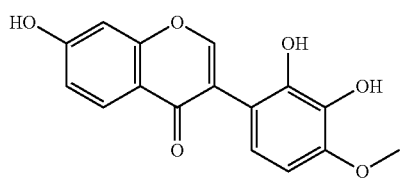 [SMILES: COc1ccc(-c2coc3cc(O)ccc3c2=O)c(O)c1O]

(also known as koparin),

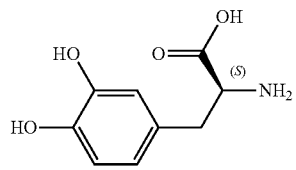

(also known as levodopa),

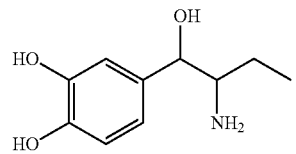

(also known as ethylnorepinephrine hydrochoride), or a pharmaceutically acceptable salt thereof. Such compounds are commercially available and also may be synthesized according to methods known in the art.

In some embodiments, the compound is an aldose reductase inhibitor. In some embodiments, an aldose reductase inhibitor is a compound that can inhibit the activity of the enzyme, aldose reductase. Aldose reductase inhibitors may reduce the flux of glucose through the polyol pathway, which can lead to inhibition of tissue accumulation of sorbitol and fructose and prevention of reduction of redox potentials. Non-limiting examples of an aldose reductase inhibitor include but are not limited to alrestatin, epalrestat, fidarestat, imirestat, lidorestat, minalrestat, ponalrestat, ranirestat, salfredin $B_{11}$, sorbinil, tolrestat, zenarestat, and zopolrestat.

In some embodiments, the aldose reductase inhibitor is Compound 1 or a pharmaceutically acceptable salt thereof.

In some embodiments, the aldose reductase inhibitor is a compound, or a pharmaceutically acceptable salt thereof, selected from: alrestatin, fidarestat, imirestat, lidorestat, minalrestat, ponalrestat, ranirestat, sorbinil, tolrestat, zenarestat, zopolrestat, epalrestat, and rhetsinine. These compounds are commercially available and also may be synthesized according to methods known in the art. These compounds have the following formulas:

| Name | Structure | Name | Structure |
|---|---|---|---|
| Alrestatin | 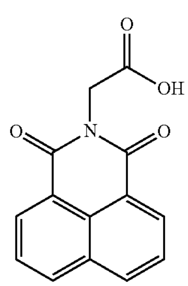 [SMILES: O=C(O)CN1C(=O)c2cccc3cccc(c23)C1=O] | Sorbinil | 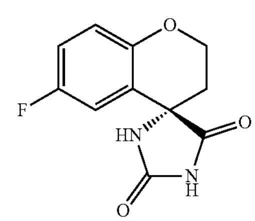 [SMILES: O=C1NC(=O)[C@@]2(CCOc3ccc(F)cc32)N1] |

-continued

| Name | Structure | Name | Structure |
|---|---|---|---|
| Fidarestat | 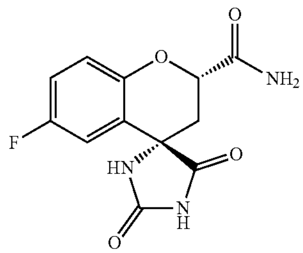 [SMILES: NC(=O)[C@@H]1C[C@]2(NC(=O)NC2=O)c2cc(F)ccc2O1] | Tolrestat | 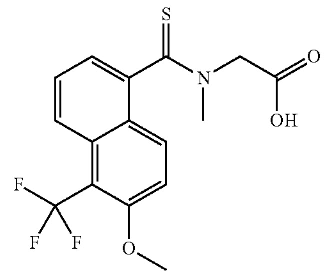 [SMILES: COc1ccc2c(C(=S)N(C)CC(=O)O)cccc2c1C(F)(F)F] |
| Imirestat | 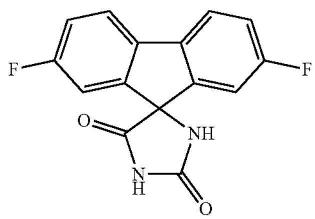 [SMILES: O=C1NC(=O)C2(N1)c1cc(F)ccc1-c1ccc(F)cc12] | Zenarestat | 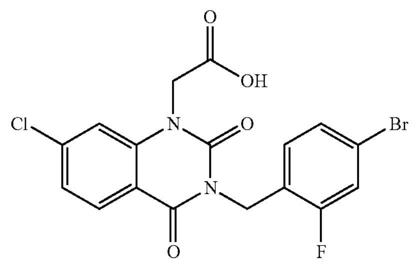 [SMILES: O=C(O)Cn1c(=O)n(Cc2ccc(Br)cc2F)c(=O)c2ccc(Cl)cc21] |
| Lidorestat | 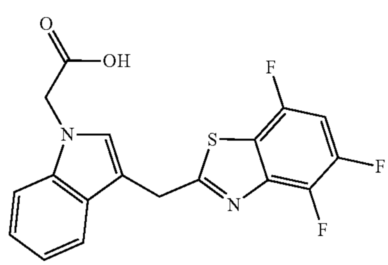 [SMILES: O=C(O)Cn1cc(Cc2nc3c(F)c(F)cc(F)c3s2)c2ccccc21] | Zopolrestat | 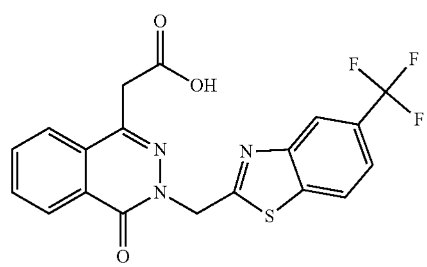 [SMILES: O=C(O)Cc1nn(Cc2nc3cc(C(F)(F)F)ccc3s2)c(=O)c2ccccc12] |
| Minalrestat | 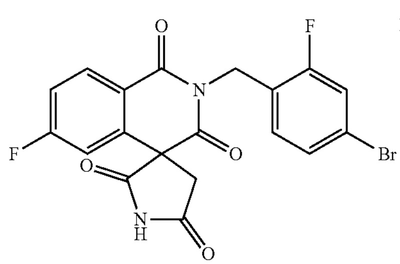 | Epalrestat | 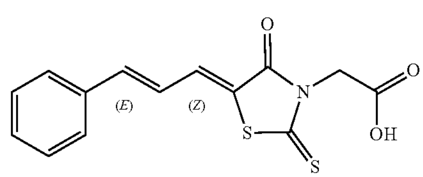 [SMILES: O=C(O)CN1C(=O)/C(=C/C=C/c2ccccc2)SC1=S] |
| Ponalrestat | 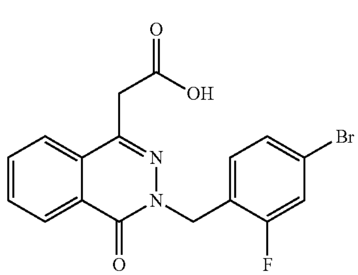 [SMILES: O=C(O)Cc1nn(Cc2ccc(Br)cc2F)c(=O)c2ccccc12] | Rhetsinine | 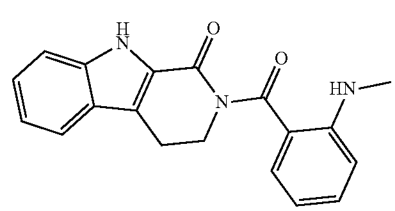 [SMILES: CNc1ccccc1C(=O)N1CCc2c([nH]c3ccccc23)C1=O] |

| Name | Structure | Name | Structure |
|---|---|---|---|
| Ranirestat | 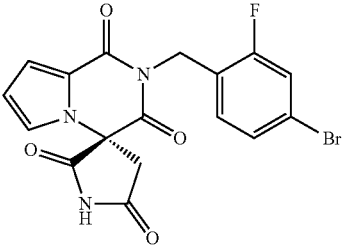 [SMILES: O=C1C[C@@]2(C(=O)N1)C(=O)N(Cc1ccc(Br)cc1F)C(=O)c1cccn12] | | |

In some embodiments, the aldose reductase inhibitor is Compound 1, epalrestat, or rhetsinine, or a pharmaceutically acceptable salt of each thereof. In some embodiments, the aldose reductase inhibitor is epalrestat.

Also provided herein, in some embodiments, are pharmaceutical compositions that comprise one or more of the compounds described herein, or a pharmaceutically acceptable salt thereof, and one or more pharmaceutically acceptable vehicles selected from carriers, adjuvants and excipients. Suitable pharmaceutically acceptable vehicles may include, for example, inert solid diluents and fillers, diluents, including sterile aqueous solution and various organic solvents, permeation enhancers, solubilizers and adjuvants. Such compositions are prepared in a manner well known in the pharmaceutical art. See, e.g., Remington's Pharmaceutical Sciences, Mace Publishing Co., Philadelphia, Pa. 17th Ed. (1985); and Modern Pharmaceutics, Marcel Dekker, Inc. 3rd Ed. (G. S. Banker & C. T. Rhodes, Eds.).

Also provided herein, in some embodiments, are pharmaceutical compositions that comprise an aldose reductase inhibitor, or a pharmaceutically acceptable salt thereof, and at least one other compound described herein, and one or more pharmaceutically acceptable vehicles selected from carriers, adjuvants and excipients.

The pharmaceutical compositions may be administered in either single or multiple doses. The pharmaceutical composition may be administered by various methods including, for example, rectal, buccal, intranasal and transdermal routes. In certain embodiments, the pharmaceutical composition may be administered by intra-arterial injection, intravenously, intraperitoneally, parenterally, intramuscularly, subcutaneously, orally, topically, or as an inhalant.

One mode for administration is parenteral, for example, by injection. The forms in which the pharmaceutical compositions described herein may be incorporated for administration by injection include, for example, aqueous or oil suspensions, or emulsions, with sesame oil, corn oil, cottonseed oil, or peanut oil, as well as elixirs, mannitol, dextrose, or a sterile aqueous solution, and similar pharmaceutical vehicles.

Oral administration may be another route for administration of the compounds described herein. Administration may be via, for example, capsule or enteric coated tablets. In making the pharmaceutical compositions that include at least one compound described herein, the active ingredient is usually diluted by an excipient and/or enclosed within such a carrier that can be in the form of a capsule, sachet, paper or other container. When the excipient serves as a diluent, it can be in the form of a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, sterile injectable solutions, and sterile packaged powders.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, sterile water, syrup, and methyl cellulose. The formulations can additionally include lubricating agents such as talc, magnesium stearate, and mineral oil; wetting agents; emulsifying and suspending agents; preserving agents such as methyl and propylhydroxy-benzoates; sweetening agents; and flavoring agents.

The compositions that include at least one compound described herein can be formulated so as to provide quick, sustained or delayed release of the active ingredient after administration to the subject by employing procedures known in the art. Controlled release drug delivery systems for oral administration include osmotic pump systems and dissolutional systems containing polymer-coated reservoirs or drug-polymer matrix formulations. Examples of controlled release systems are given in U.S. Pat. Nos. 3,845,770; 4,326,525; 4,902,514; and 5,616,345. Another formulation for use in the methods disclosed herein employ transdermal delivery devices ("patches"). Such transdermal patches may be used to provide continuous or discontinuous infusion of the compounds described herein in controlled amounts. The construction and use of transdermal patches for the delivery of pharmaceutical agents is well known in the art. See, e.g., U.S. Pat. Nos. 5,023,252, 4,992,445 and 5,001,139. Such patches may be constructed for continuous, pulsatile, or on demand delivery of pharmaceutical agents.

For preparing solid compositions such as tablets, the principal active ingredient may be mixed with a pharmaceutical excipient to form a solid preformulation composition containing a homogeneous mixture of a compound described herein. When referring to these preformulation compositions as homogeneous, the active ingredient may be dispersed evenly throughout the composition so that the composition may be readily subdivided into equally effective unit dosage forms such as tablets, pills and capsules.

The tablets or pills of the compounds described herein may be coated or otherwise compounded to provide a dosage form affording the advantage of prolonged action, or to protect from the acid conditions of the stomach. For example, the tablet or pill can include an inner dosage and an outer dosage component, the latter being in the form of an envelope over the former. The two components can be separated by an enteric layer that serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

Compositions for inhalation or insufflation may include solutions and suspensions in pharmaceutically acceptable, aqueous or organic solvents, or mixtures thereof, and powders. The liquid or solid compositions may contain suitable pharmaceutically acceptable excipients as described herein. In some embodiments, the compositions are administered by the oral or nasal respiratory route for local or systemic effect. In other embodiments, compositions in pharmaceutically acceptable solvents may be nebulized by use of inert gases. Nebulized solutions may be inhaled directly from the nebulizing device or the nebulizing device may be attached to a facemask tent, or intermittent positive pressure breathing machine. Solution, suspension, or powder compositions may be administered, preferably orally or nasally, from devices that deliver the formulation in an appropriate manner.

Kits

Provided herein are also kits that include a compound of the disclosure and suitable packaging. In one embodiment, a kit further includes instructions for use. In one aspect, a kit includes a compound of the disclosure and a label and/or instructions for use of the compounds in the treatment of the indications, including the diseases or conditions, described herein.

Provided herein are also articles of manufacture that include a compound described herein in a suitable container. The container may be a vial, jar, ampoule, preloaded syringe, and intravenous bag.

Treatment Methods and Uses

A congenital disorder of glycosylation (CDG) is associated with deficient or defective glycosylation of various tissue proteins or lipids. Individuals with a CDG are missing an enzyme required for glycosylation. The type of CDG depends on which enzyme is missing.

Phosphomannomutase deficiency disease (PMM2 or PMM2-CDG, and also previously known as CDG-Ia) is a rare congenital disorder of glycosylation with no cure. It is an autosomal recessive disorder arising from a dysfunctional phosphomannomutase-2 gene. The phosphomannomutase-2 enzyme is responsible for transforming mannose 6-phosphate into mannose 1-phosphate which in turn leads to the synthesis of GDP-mannose. Insufficient levels of GDP-mannose leads to under-glycosylated glycoproteins, lysosomal enzymes and serum proteins. PMM2-CDG is the most common disorder of glycosylation with more than 800 patients reported worldwide. Clinical presentation of patients varies widely but almost all patients suffer from neuromuscular abnormalities, developmental delays, failure to thrive and multiple organ system involvement from liver to kidneys. Diagnosis occurs in early infancy due to repetitive medical problems associated with failure to thrive and grow according to normal milestones.

Over 116 mutations, mostly missense mutations, have been associated with Pmm-2 disease. However, very few individuals with CDG's have homozygous mutations compared to compound heterozygous mutations. It has been proposed that homozygous mutations are either lethal or confer sub-clinical phenotypes associated with residual enzyme activity. In other words, a complete lack of pmm-2 enzyme activity is incompatible with life. Individuals with 50% enzyme activity are asymptomatic whereas individuals with 25% or less enzyme activity show varying levels of disease presentations.

Provided herein are methods for treating increasing glycosylation in a patient in need thereof comprising administering a therapeutically effective amount of a compound as described herein, or a combination of the compounds described herein, or a composition as described herein.

In some embodiments, increasing glycosylation provides increased levels of glycosylated glycoproteins, lysosomal enzymes, or serum proteins as compared to levels of glycoproteins, lysosomal enzymes, or serum proteins prior to administration. Measurement of glycosylated glycoproteins, lysosomal enzymes, or serum proteins are methods known in the art. See, e.g., Carchon et al., Clinical Chemistry, 50:1, 101-111 (2004).

Provided herein are methods for treating a condition or disorder mediated, at least in part, by phosphomannomutase-2 enzyme in a patient in need thereof comprising administering a therapeutically effective amount of a compound as described herein, or a combination of the compounds described herein, or a composition as described herein.

In some embodiments, the condition or disorder mediated, at least in part, by phosphomannomutase-2 enzyme, is a congenital disorder of glycosylation. In some embodiments, the congenital disorder of glycosylation is a Type I disorder (e.g. Ia, Ib, Ic, Id, Ie, If, Ih, Ii, Ij, Ik, IL, Im, In, Io, Ip, Iq, Ir, DPM2-CDG, TUSC3-CDG, MAGT1-CDG, DHDDS-CDG, and I/IIx). In some embodiments, the congenital disorder of glycosylation is a Type II disorder (e.g. IIa, IIb, IIc, IId, IIe, IIf, IIg, IIh, IIi, IIj, IIL, ATP6V0A2-CDG, MAN1B1-CDG, and ST3GAL3-CDG).

In some embodiments, the congenital disorder of glycosylation is phosphomannomutase deficiency.

Provided herein are methods for treating a congenital disorder of glycosylation in a patient in need thereof comprising administering a therapeutically effective amount of a compound as described herein, or a combination of the compounds described herein, or a composition as described herein.

In some embodiments, the congenital disorder of glycosylation is a Type I disorder. In some embodiments, the congenital disorder of glycosylation is a Type II disorder.

In some embodiments, the congenital disorder of glycosylation is phosphomannomutase deficiency.

Provided herein are method for treating phosphomannomutase deficiency in a patient in need thereof comprising administering a therapeutically effective amount of a compound as described herein, or a combination of the compounds described herein, or a composition as described herein.

It is contemplated herein that, in some embodiments, a compound described herein may be useful for treating congenital disorders of deglycosylation (CDDG).

In some embodiments, a compound described herein may be useful for treating NGLY1-related congenital disorder of deglycosylation (NGLY1-CDDG).

In any of the embodiments described herein, a patient is administered one or more of the compounds described herein. The one or more compounds can be administered simultaneously or sequentially.

In any of the embodiments described herein, a patient is administered a pharmaceutical composition that comprises one or more of the compounds described herein.

In any of the embodiments described herein, the patient is further administered a therapeutically effective amount of another therapeutic agent.

In any of the embodiments described herein, the patient is further administered a therapeutically effective amount of another therapeutic agent useful for increasing glycosylation. In some embodiments, the therapeutic agent is mannoform phosphate.

In any of the embodiments described herein, the patient is further administered a therapeutically effective amount of another therapeutic agent, wherein the therapeutic agent is an aldose reductase inhibitor.

The another therapeutic agent may be administered simultaneously or sequentially with a compound, or compounds, described herein or a composition described herein.

Dosing

The specific dose level of a compound of the present disclosure for any particular subject will depend upon a variety of factors including the activity of the specific compound employed, the age, body weight, general health, sex, diet, time of administration, route of administration, and rate of excretion, drug combination and the severity of the particular disease in the subject undergoing therapy. For example, a dosage may be expressed as a number of milligrams of a compound described herein per kilogram of the subject's body weight (mg/kg). Dosages of between about 0.1 and 150 mg/kg may be appropriate. In some embodiments, about 0.1 and 100 mg/kg may be appropriate. In other embodiments a dosage of between 0.5 and 60 mg/kg may be appropriate. Normalizing according to the subject's body weight is particularly useful when adjusting dosages between subjects of widely disparate size, such as occurs when using the drug in both children and adult humans or when converting an effective dosage in a non-human subject such as dog to a dosage suitable for a human subject.

The daily dosage may also be described as a total amount of a compound described herein administered per dose or per day. Daily dosage of a compound described herein may be between about 1 mg and 4,000 mg, between about 2,000 to 4,000 mg/day, between about 1 to 2,000 mg/day, between about 1 to 1,000 mg/day, between about 10 to 500 mg/day, between about 20 to 500 mg/day, between about 50 to 300 mg/day, between about 75 to 200 mg/day, or between about 15 to 150 mg/day.

When administered orally, the total daily dosage for a human subject may be between 1 mg and 1,000 mg, between about 1,000-2,000 mg/day, between about 10-500 mg/day, between about 50-300 mg/day, between about 75-200 mg/day, or between about 100-150 mg/day.

The compounds of the present disclosure or the compositions thereof may be administered once, twice, three, or four times daily, using any suitable mode described above. Also, administration or treatment with the compounds may be continued for a number of days; for example, commonly treatment would continue for at least 7 days, 14 days, or 28 days, for one cycle of treatment. Treatment cycles are well known, and are frequently alternated with resting periods of about 1 to 28 days, commonly about 7 days or about 14 days, between cycles. The treatment cycles, in other embodiments, may also be continuous.

In a particular embodiment, the method comprises administering to the subject an initial daily dose of about 1 to 800 mg of a compound described herein and increasing the dose by increments until clinical efficacy is achieved. Increments of about 5, 10, 25, 50, or 100 mg can be used to increase the dose. The dosage can be increased daily, every other day, twice per week, or once per week.

EXAMPLES

The following examples are included to demonstrate specific embodiments of the disclosure. It should be appreciated by those of skill in the art that the techniques disclosed in the examples which follow represent techniques to function well in the practice of the disclosure, and thus can be considered to constitute specific modes for its practice. However, those of skill in the art should, in light of the present disclosure, appreciate that many changes can be made in the specific embodiments which are disclosed and still obtain a like or similar result without departing from the spirit and scope of the disclosure.

General Methods

Strains and Plasmids

All strains used herein are in S288c background. Strains were grown in Synthetic Complete ("SC") or SC drop out media (Sunrise)+2% dextrose at 30° C. unless otherwise noted. Standard genetic procedures of transformation and tetrad analysis were followed to construct strains. SEC53 rescue plasmid (pPL1) was generated by cloning the SEC53 promoter, open reading frame, and terminator sequences into the episomal pRS316 containing the URA3 selectable marker. SEC53 variants were generated by cloning the relevant promoter, GFP or SEC53 gene, and CYC1 terminator sequences into an integrating plasmid containing the LEU2 selectable marker and integrated at the SwaI restriction site into the HO locus. For PMM2 variants, the SEC53 ORF was replaced with a codon-optimized PMM2. Plasmids were generated by Next Interactions or GenScript. Strains were generated by Next Interactions or well-known techniques.

Growth Assay

Cells from plates were resuspended in SC media to $OD_{600}=1.0$, then serial diluted into 50 µL SC+FOA media in 384-well plates at $10^{-1}$, $10^{-2}$, and $10^{-3}$. Plates were incubated at 30° C. and absorbance reading at 600 nM were measured by a plate reader (Molecular Devices SpectraMax M3) at the indicated time points. Plates were vortexed briefly to resuspend cells prior to plate readings. 5-floroortic acid was purchased from US Biological and used at a concentration of 1 mg/L.

PMM2 Enzymatic Assay

Yeast lysis: yeast lysates were prepared from 50 $OD_{600}$'s worth of cells. Cells are washed once in 25 mM $KPO_4$ pH 8.0 and resuspended in 600 µL lysis buffer (25 mM Tris-HCl pH 7.5, 1 mM EDTA, 100 mM NaCl, 10 mM β-mercaptoethanol, and 1 Roche protease inhibitor tablet) and an equivalent amount of glass beads. The bead/lysate mixture was vortexed for 7-10 cycles of 2 mM vortex and 1 mM cooling on ice. Lysis was checked by microscopy to confirm that 80-95% of cells are lysed. The lysates were clarified by 15 mins centrifuge at max speed at 4° C. and the supernatant moved to a new tube. For long term storage at −80° C., glycerol was added to 20% of the total volume. Protein concentration was determined with the Qubit protein assay kit (Thermo Fisher Scientific).

Cells (WT and PMM2 (GM20942-R141H/F119L) compound heterozygous fibroblasts) were seeded at 45 cells/µL (48 hours) and 60 cells/µL (24 hours) in 96 well plates. Compounds were added while seeding cells. The cells were incubated with the tested compounds for 24 and 48 hours (2 different plates, at 10 and 15 µM). Cells were washed twice with phosphate buffer solution. Cell extracts were prepared by adding 10 µL homogenization buffer (20 mM Hepes, 25 mM KCl, 1 mM dithiothreitol, 10 µg/mL each leupeptin and antipain) into each well. The plate was frozen at −80° C. and thawed (this step was repeated two times). Contents of the well were then transferred to the next well, frozen, and thawed. The previous two steps were repeated again to obtain 3× protein. The plate was centrifuged at 4000 rpm for 10 min. 1 µL of sample was taken for Qubit protein quantification, and assay buffer was added into these wells. The plate was incubated at 37° C., and readings were taken every 30 mins.

Fibroblast Cell Lysis

PMM2 enzymatic activities were assayed spectrophotometrically at 340 nm by the reduction of NADP+ to NADPH in a reaction mixture incubated at 30° C. for 60 mins in a 96-well plate. Cell lysates were added to 200 µL volume in the following reaction: 50 mM HEPES, pH 7.1, 5 mM $MgCl_2$, 0.5 mM NADP+, 10 µg/mL yeast glucose-6-phosphate dehydrogenase, 20 µM glucose 1,6-bisphosphate, 200 µM mannose 1-phosphate, 10 µg/mL phosphoglucose isomerase, and 5 phosphomannose isomerase. Glucose 1,6-bisphosphate was used as an activator of PMM2 activity. NADPH formation was calculated from absorbance at 340 nm using the Beer's Law (absorbance=εLc).

Drug Screen 125 nL of compounds or DMSO were dispensed into 384-well plates using the Echo acoustic dispenser (LabCyte) to achieve a final concentration of 25 µM. 50 µL of $10^{-2}$ dilution of an $OD_{600}$=1.0 or 0.5 yeast cell suspensions were dispensed into the 384-well plates containing compounds or DMSO with a MultiFlo automated dispenser (Biotek). Plates were covered and incubated at 30° C. for 16-21 hours until $OD_{600}$ reaches ~0.8. Plates were vortexed briefly to resuspend cells prior to reading.

Validation

MicroSource Spectrum compounds were reordered from MicroSource Discovery Systems and resuspended in DMSO. 5-125 nL compounds or DMSO were dispensed into 384-well plates and 50 µL of yeast cell suspensions or media were dispensed by multichannel pipettes to achieve the desired concentration. Plates were covered and incubated at 30° C. for 16-23 hours until $OD_{600}$ reaches ~0.8. Plates were vortexed briefly to resuspend cells prior to plate readings.

Example 1: Yeast Mutant Models of PMM2 Disease

Modeling PMM2 Patient Alleles in Yeast SEC53

Mammalian PMM2 and the yeast homolog, SEC53 shares 55% identity at the amino-acid level. Three common PMM2 disease-causing alleles (R141H, F119L, and V231M) and two less well studied alleles (E93A and E139K) were generated. R141 is in the substrate binding domain of PMM2. R141H has no detectable enzymatic activity and never occurs in homozygosity in patients. F119 is a component of the hydrophobic core within the dimer interface. F119L has 25% enzymatic activity and this deficiency is likely due to its diminished ability to dimerize. V231 is in the interior of the core domain and a mutation in this residue is detrimental to its native structure. This folding and stability defect of the V231M allele contributes to its reduced activity of 38.5%.

Existing data on E93A and E139K variants are limited. E93 directly interacts with R116 in trans within the PMM2 dimer and a mutation in this residue likely compromise dimerization. E139K is a result of a 415G>A mutation in the DNA sequence that interferes with RNA splicing. This causes either skipping of exon 5 to form a partially deleted and nonfunctional protein or a full-length E139K protein.

PMM2 F119L, R139K, R141H, and V231M correspond to SEC53 F126L, E146K, R148H, and V238M, respectively. SEC53 E100K was unintentionally generated, but the residue is conserved in PMM2 and the patient allele is E93A. Many of these variants have low to no detectable enzymatic activity, so the mutants were placed under different promoters to determine if changes in protein abundance affect viability of each variant. The relative strength of the TEF1, ACT1, and REV1 promoters were compared to the native SEC53 promoter by driving expression of the green fluorescent protein (GFP). Based on fluorescence reading by flow cytometry, it was determined that, relative to SEC53, the strength of TEF1, ACT, and REV1 are 10×, 2×, and 0.2×, respectively.

Growth of Sec53 Variants Correlate with the Enzymatic Defects of the Variant and the Promoter Strength To overcome the complication that SEC53 is an essential gene, a wild type SEC53 copy was placed on a URA3 plasmid that we can conditionally remove by growing cells in 5-fluoroorotic acid (5-FOA). 5-FOA is an analog of uracil that is converted into a toxic intermediate in cells where the uracil biosynthetic pathway is active, which the URA3 marker enables. Each SEC53 variant is then individually integrated at the HO locus of sec53Δ cells. The phenotype of each variant is revealed when the wild type URA3 containing plasmid is counter-selected in media containing 5-FOA.

Increasing the expression level of the hypomorphic alleles improve their growth. The V238M allele when expressed at native level is sufficient for growth, but much slower than wild type cells (31.8%). Doubling the expression of the V238M allele with the ACT1 promoter strongly restore growth of this mutant (67% at 20 hours and near wild type level at 24 hour). The F126L allele grows poorly under the endogenous promoter (26.9%), and also grows better when its expression is doubled (56.6%). The relative growth of F126L and V238M is are consistent with their reported in vitro enzymatic activity. Over-expression of F126L and V238M alleles under the TEF1 promoter completely rescues these cells. E100K is viable only under the ACT1 (16.2%) and TEF1 (66.5%) promoters, which indicates the severity of this mutation. On the other hand, the R148H null allele is not sufficient for growth at any promoter strength and mimics sec53Δ. Together, these data can be fully explained by mass action effects, where a reduction in enzymatic activity can be overcome by increasing the total amount of enzyme.

In contrast, reducing the wild type level to 20% of its native level with the REV1 promoter modestly, but consistently, compromises cell growth to 63.6%. This indicates that cells are highly sensitive to the total amount of SEC53 protein. Similar to wild type, E146K variant is defective only at very low expression under the REV1 promoter (68.8%). This suggests that the splicing defect of the 415G>A mutation in human may reduce the abundance of functional E139K proteins to an amount insufficient for normal growth.

Comparing the strains relative to one another at a single time-point, the severity of growth defects of the SEC53 alleles correlate with the level of enzymatic activity of the PMM2 alleles. In other words, the genotype-phenotype relationship is conserved between yeast and humans.

SEC53 Diploid Variants Recapitulate the Growth of Haploid Variants

Most PMM2-CDG patients have compound heterozygous mutations that is most commonly paired with the R141H null allele. To further study the nature of the PMM2 variants, homozygous and heterozygous diploids were generated. As expected, a single copy of wild type SEC53 is sufficient for normal growth and there is no growth difference between homozygous wild type and heterozygous wild type/R148H (99.7%).

Homozygous F126L diploids grow slower than their respective F126L/R148H heterozygous diploids. At 20 hours, the growth of pACT-F126L/F126L is 51.8% compared to 65.7% in pACT1-F126L/R148H. pSEC53-F126L/F126L is 20.9% compared to 40.7% in pSEC53-F126L/R148H. It is contemplated that these results may be explained by the diminished ability of PMM2 F119L variant to dimerize and the presence of R141H may facilitate formation of heterodimers. On the other hand, pSEC53-V238M/V238M homozygous diploid (43.2%) grows similarly to the pSEC53-V238M/R148H heterozygous diploid (46.4%).

E100K homozygous diploids grow poorer than its E100K/R148H heterozygous diploids, which in turns grow slower than the E100K/WT diploids. Under the TEF1 promoter, E100K/E100K is 53.4% compared to 98.8% in E100K/WT and 100% in E100K/R148H. Under the ACT1 promoter, E100K/E100K is 8.2% compared to 100% in E100K/WT and 77.9% in E100K/R148H. Like F126, E100 is expected to affect dimerization and R148H may facilitate the formation of partially functional dimers. E146K is indistinguishable from wild type cells except at the lowest expression level. Oddly, pREV1-E146K homozygous diploids (65.6%) grew poorly compared to its E146K/R148H heterozygous diploids (96.2%).

The Phenotypes of Human PMM2 Alleles in Yeast Parallel SEC53 Alleles

It has previously been shown that expression of human PMM2 rescues a temperature-sensitive allele of SEC53, sec53-6. PMM2 cDNA was originally expressed, and this failed to rescue yeast sec53Δ. Expression of PMM2 that is codon-optimized for expression in yeast does in fact rescue sec53Δ. Subsequently, each of the PMM2 variant in sec53Δ cells were expressed to determine whether PMM2 alleles behave the same as SEC53 alleles. Under the SEC53 promoter, PMM2 partially rescues sec53Δ to 71% of wild type yeast SEC53. The degree to which each PMM2 variant rescues sec53Δ correlates with their enzymatic activity and supports the conserved genotype-phenotype relationship. PMM2 E139K (68%) grow similarly to wild type PMM2, in agreement with yeast SEC53 E146K. V231M compromises growth (55.6%) and F119L further compromises growth (44.8%). E93A, on the other hand, is not sufficient for growth under the SEC53 promoter and does not restore growth above sec53Δ cells. This is consistent with pSEC53-E100K and further supports the significance of E93 in PMM2 function.

Expressing PMM2 under the ACT1 promoter improves growth to 97.3%. Expectedly, doubling the expression of F119L with the ACT1 promoter also improves its growth to 63.6%. Under the TEF1 promoter, PMM2 completely rescues sec53Δ cells. This suggests that PMM2 expressed in yeast may not be functioning at optimal level and requires higher expression level. However, we can determine the deficiency of a given PMM2 allele in yeast.

Enzymatic Activity in Cell Lysate is not Reflected by Growth of Cells

A PMM2 enzymatic assay was performed to determine whether the expression level of the variants correlate with the enzymatic activity in the cell. To do this, phosphomannose mutase (PMM) activity was assayed by measuring the reduction of NADP+ to NADPH spectrophotometrically at 340 nm with a plate reader according to methods known in the art. This is achieved by a series of four reactions shown in Scheme 1.

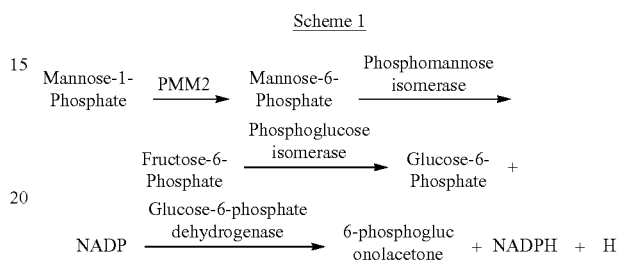

Scheme 1

Mannose-1-phosphate and NADP are provided as substrates for the reactions along with phosphomannose isomerase, phosphoglucose isomerase, glucose-6-phosphoate dehydrogenase, and PMM2 from the protein lysate. Additionally, glucose 1,6-bisphosphate is used as an activator of PMM2 activity.

Example 2: Compounds for PMM2-CDG

Drug Screen in Yeast Models of PMM2-CDG Identified Three Chemical Modifiers pACT1-F126L, pSEC53-V238M, and pSEC53-F126L haploids and pACT1-F126L/pACT1-R148H, pSEC53-V238M/pSEC53-R148H, and pSEC53-F126L/pSEC53-R148H heterozygous diploids were advanced to a high-throughput drug screen. Screening was done in a 2,560 compound MicroSource Spectrum library collection consisting of FDA approved drugs, bioactive tool compounds, and natural products. Each strain was screened in duplicate and in 384-well plates, with each plate containing 32 wells of the negative control (no drugs) and 24 wells of the positive controls (wild type cells). The positive and negative controls showed good separation of the Z-scores, which allowed distinguishing a rescue of growth in the screen. Additionally, there is good correlation between replicates (correlation >0.4 for all panels). With a Z-score cutoff of 2.0, we initially identified six compounds that may be promising and their ability to rescue growth is conserved between the haploid and diploid strains.

These initial hits were further studied for validation. It was found that three of these initial six compounds (specifically Compound 1, Compound 2, and Compound 3) showed consistent and dose-dependent rescues in haploid and heterozygous diploid cells (FIG. 1A, FIG. 1B, and FIG. 1C and FIG. 2A, FIG. 2B, and FIG. 2C). The negative control compound cysteamine hydrochloride does not rescue at any dose (FIG. 1D and FIG. 2D). At the maximum dose tested, alpha-cyano-4-hydroxycinnamic acid (Compound 1) rescues the F126L allele by 17.7% in haploid and 24.5% in diploid cells. Interestingly, this rescue was specific to the 2X pACT1 level (FIG. 1A and FIG. 2A).

Figure 2B:
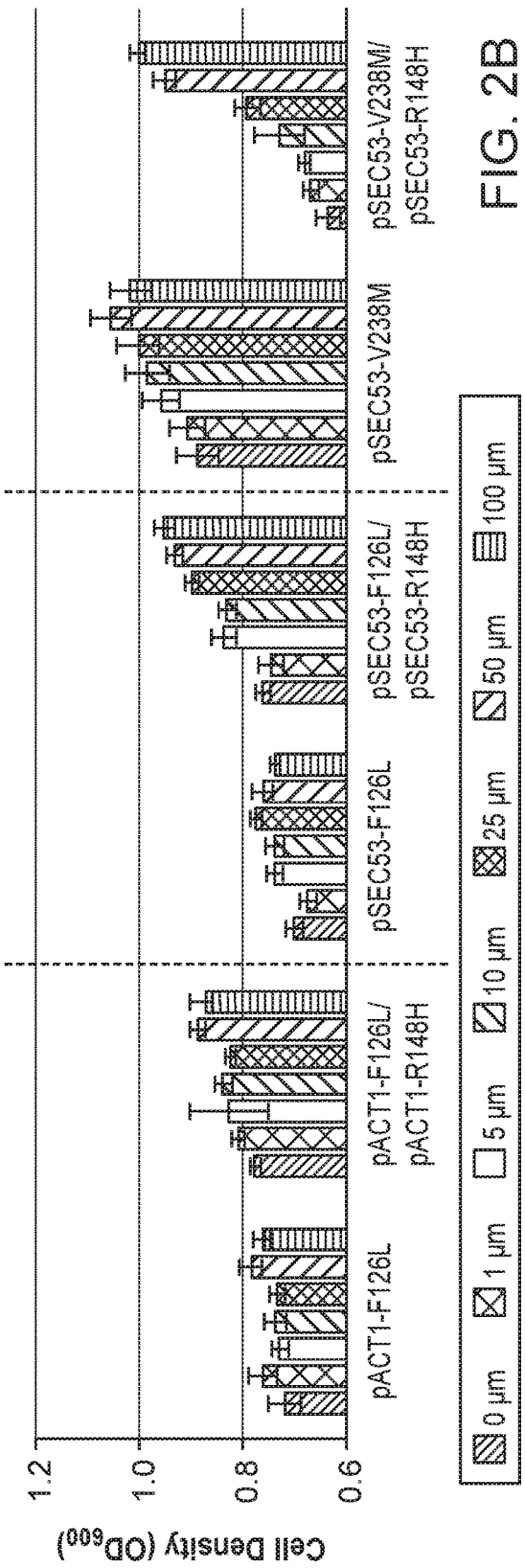

2'-2'-bisepigallocatechin digallate (Compound 2) rescues growth of pSEC53-F126L and pSEC53-V238M cells, and pACT1-F126L to a much lesser extent (FIG. 1B and FIG. 2B). Compound 2 also exerts a stronger response in heterozygous diploid cells than haploids. Growth of pSEC53-F126L improved by as much as 10.6% and pSEC53-F126L/R148H by 25%. pSEC53-V238M improved by 14.6% and pSEC53-V238M/R148H by 57.7%. pACT1-F126L cells only improved by 6.3% and 12.9% in pACT1-F126L/R148H (FIG. 1B and FIG. 2B).

Figure 2C:
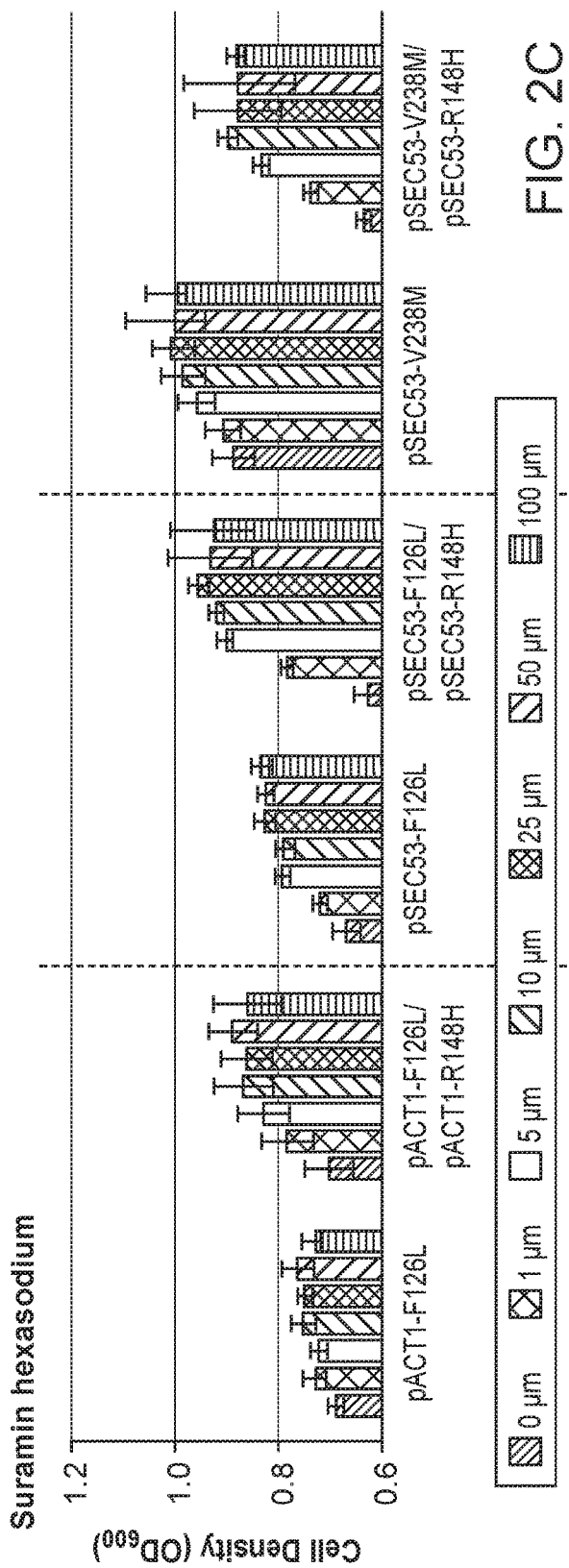
Figure 2D:
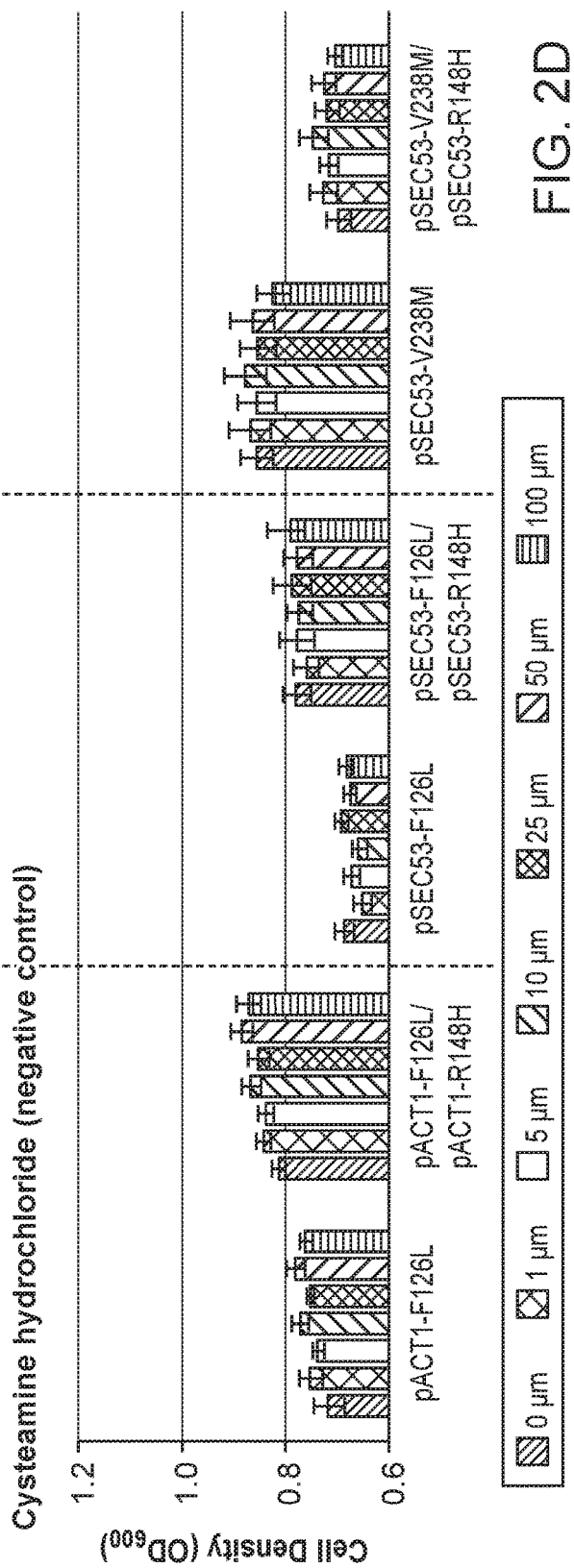
Figure 3:
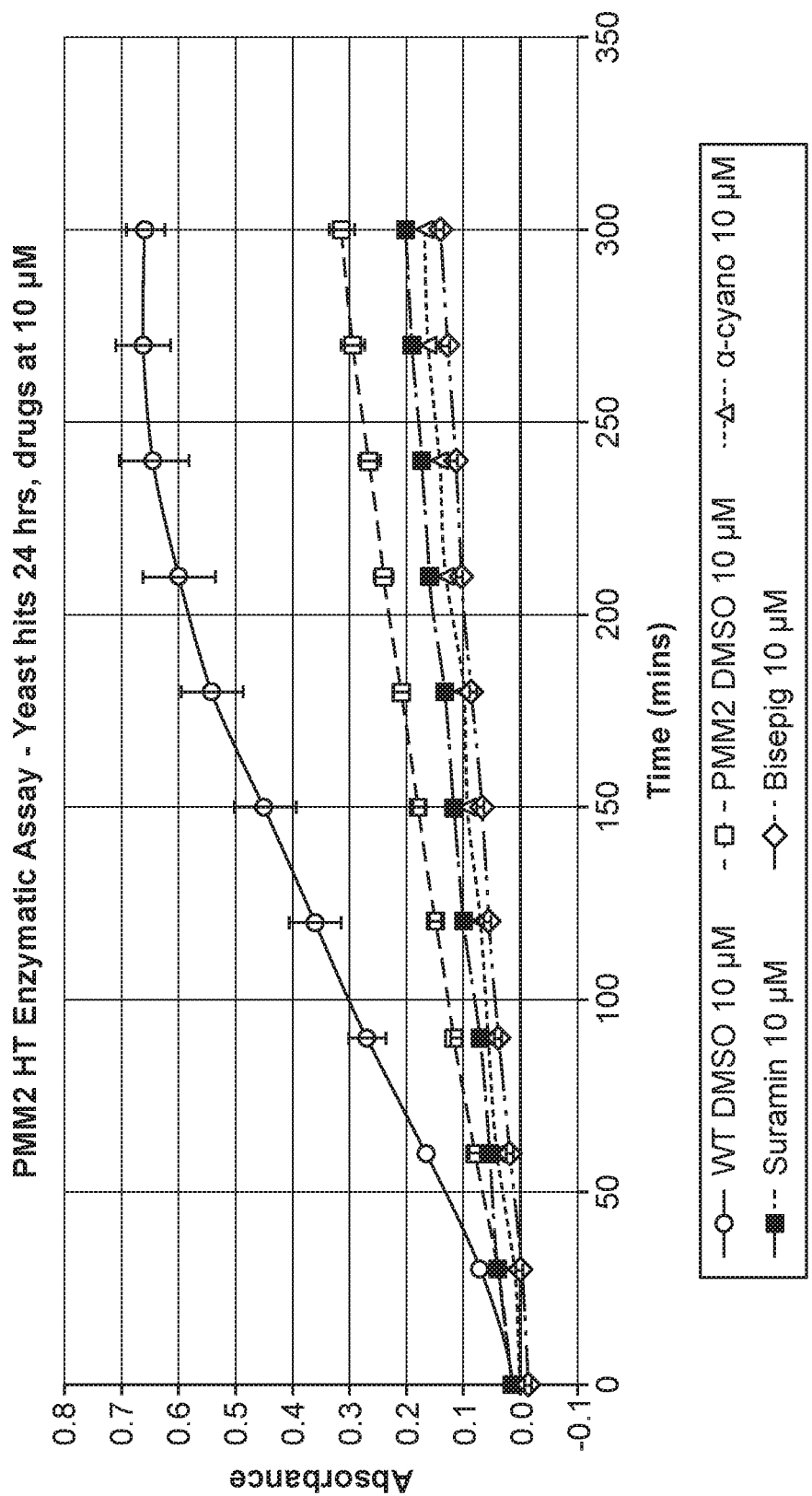
FIG. 3 illustrates a comparison of the absorbance of the following compounds, each at a concentration of 10 μM, in a PMM2 HT Enzymatic Assay after 24 hours: Wild Type ("WT DMSO"); PMM2 compound heterozygous mutant R141H/F119L ("PMM2 DMSO"); Compound 1 ("α-cyano"); hexasodium salt of Compound 3 ("suramin"); and Compound 2 ("bisepig).
Figure 4:
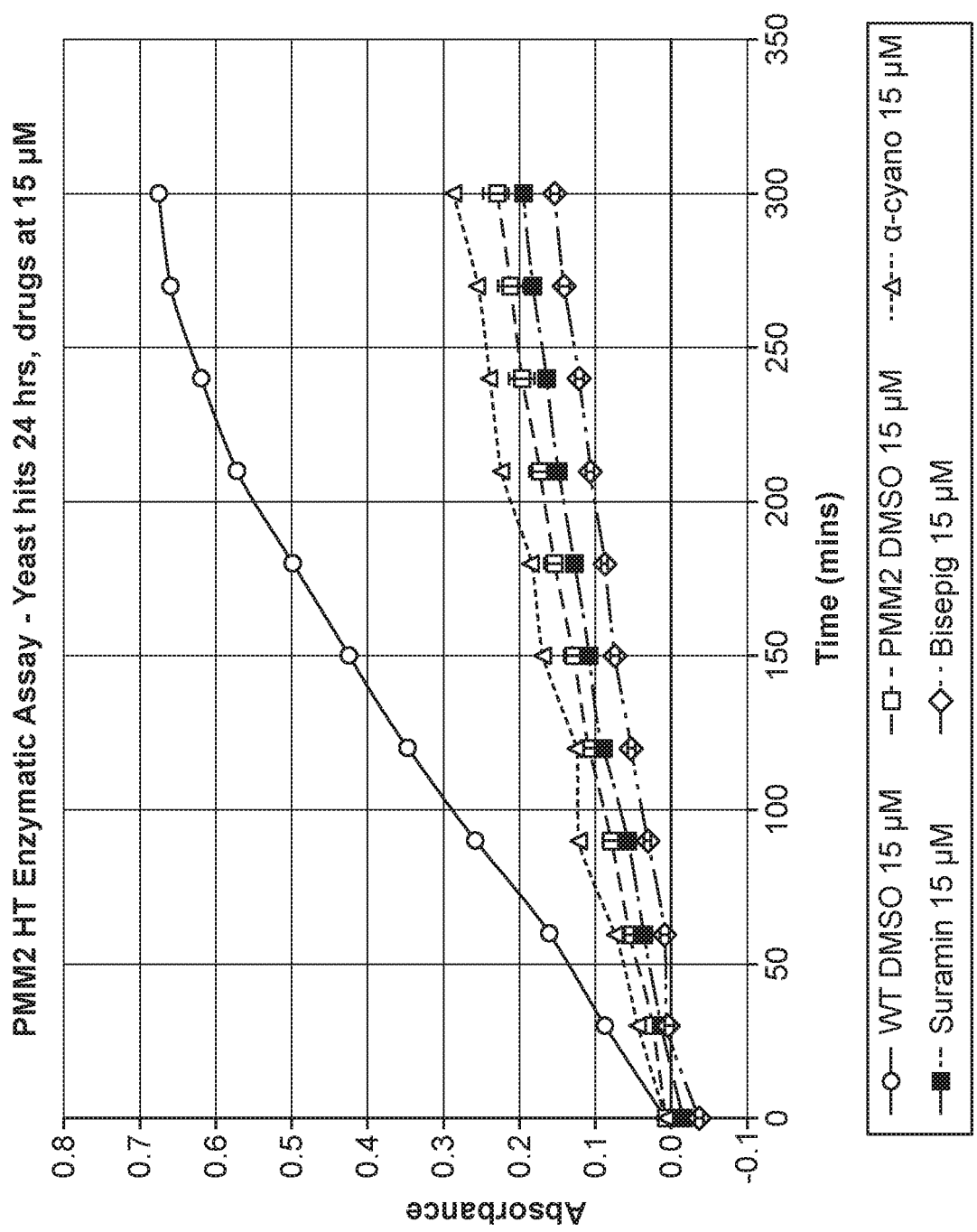
FIG. 4 illustrates a comparison of the absorbance of the following compounds, each at a concentration of 15 μM, in a PMM2 HT Enzymatic Assay after 24 hours: Wild Type ("WT DMSO"); PMM2 compound heterozygous mutant R141H/F119L ("PMM2 DMSO"); Compound 1 ("α-cyano"); hexasodium salt of Compound 3 ("suramin"); and Compound 2 ("bisepig).
Figure 5:
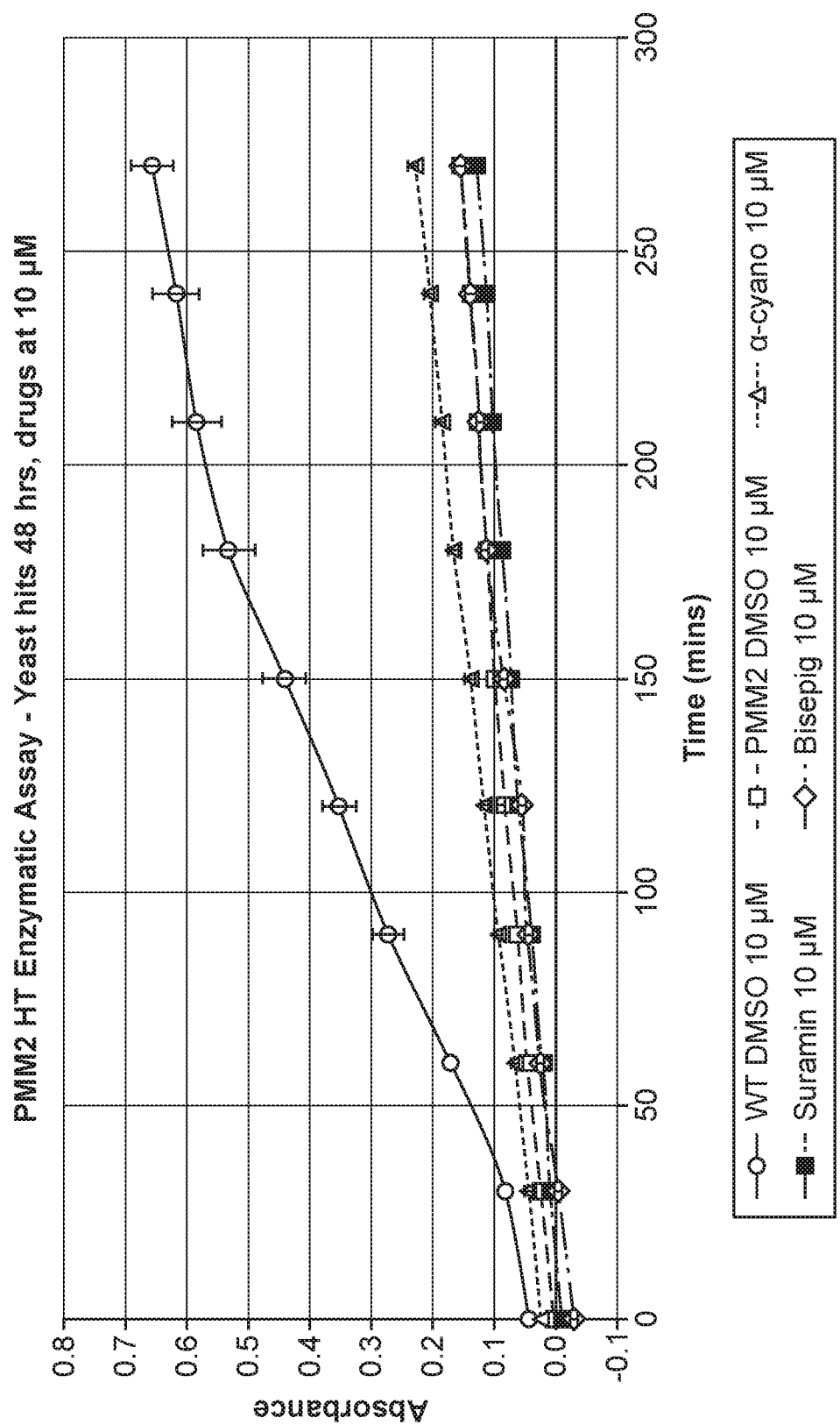
FIG. 5 illustrates a comparison of the absorbance of the following compounds, each at a concentration of 10 μM, in a PMM2 HT Enzymatic Assay 48 hours: Wild Type ("WT DMSO"); PMM2 compound heterozygous mutant R141H/F119L ("PMM2 DMSO"); Compound 1 ("α-cyano"); hexasodium salt of Compound 3 ("suramin"); and Compound 2 ("bisepig).
Figure 6:
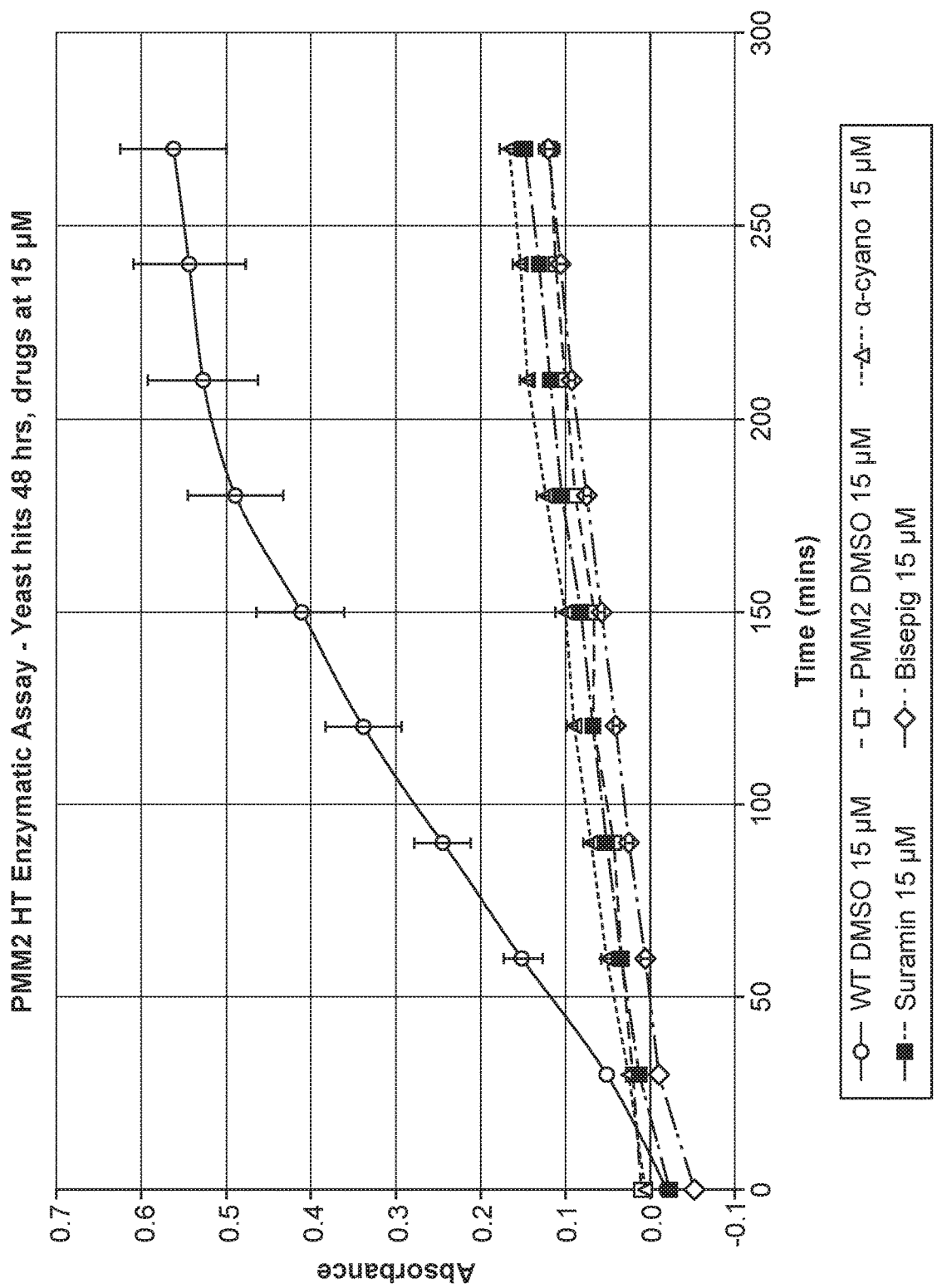
FIG. 6 illustrates a comparison of the absorbance of the following compounds, each at a concentration of 15 μM, in a PMM2 HT Enzymatic Assay after 48 hours: Wild Type ("WT DMSO"); PMM2 compound heterozygous mutant R141H/F119L ("PMM2 DMSO"); Compound 1 ("α-cyano"); hexasodium salt of Compound 3 ("suramin"); and Compound 2 ("bisepig).
Figure 7A:
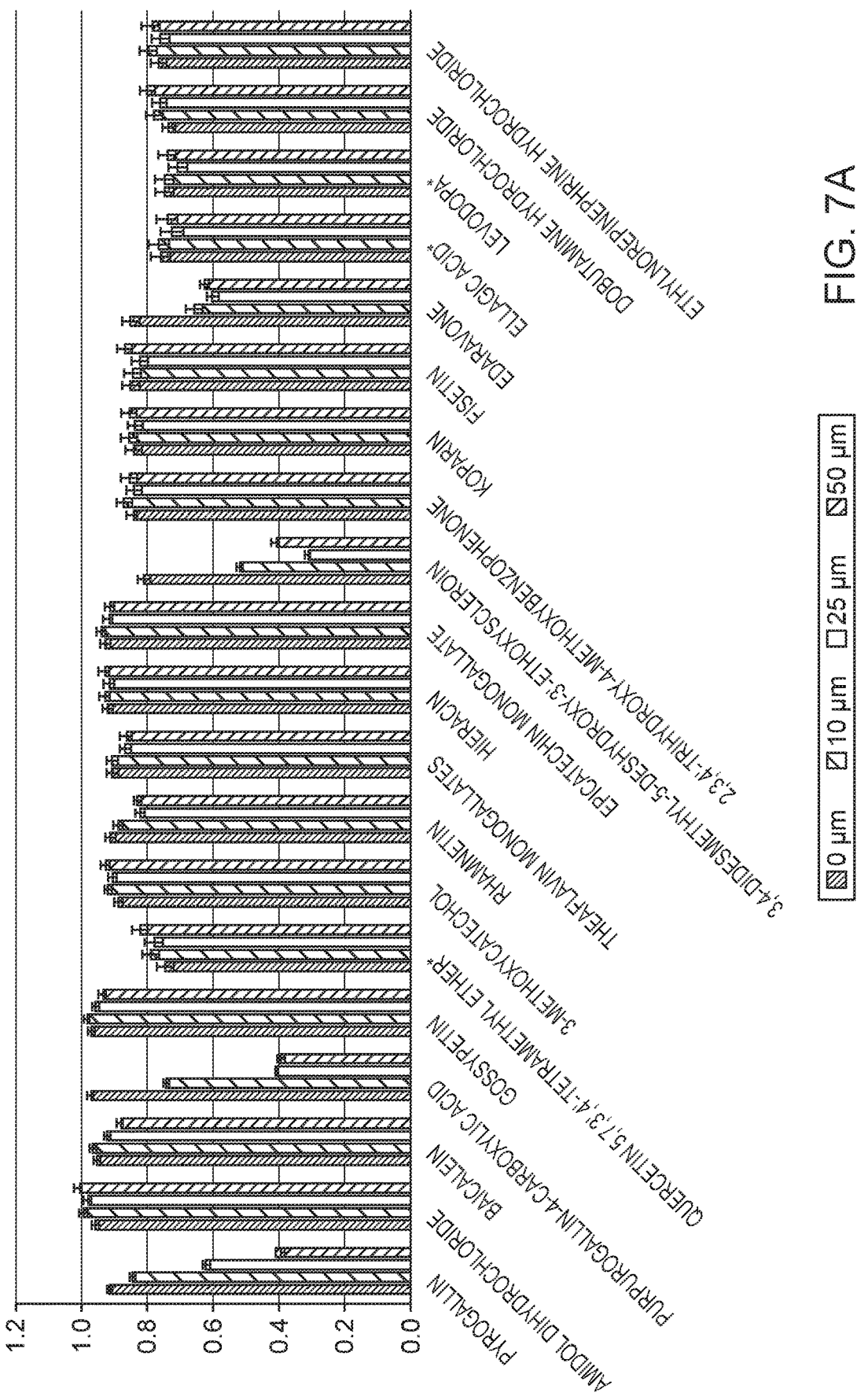
FIG. 7A illustrates a comparison of the absorbance at 600 nm of the following compounds, at concentrations of 0 μM, 10 μM, 25 μM, and 50 μM, in pACT1-F126L/R148H (PLY65) cells: pyrogallin, amidol dihydrochloride, baicalein, purpurogallin-4-carboxylic acid, gossypetin, quercetin 5,7,3',4'-tetramethyl ether, 3-methoxycatechol, rhamnetin, theaflavin monogallates, hieracin, epicatechin monogallate, 3,4-didesmethyl-5-deshydroxy-3'-ethoxysclerion, 2,3,4'-trihydroxy-4-methoxybenzophenone, koparin, fiestin, edaravone, ellagic acid, levodopa, dobutamine hydrochloride, and ethylnorepinephrine hydrochloride.
Figure 7B:
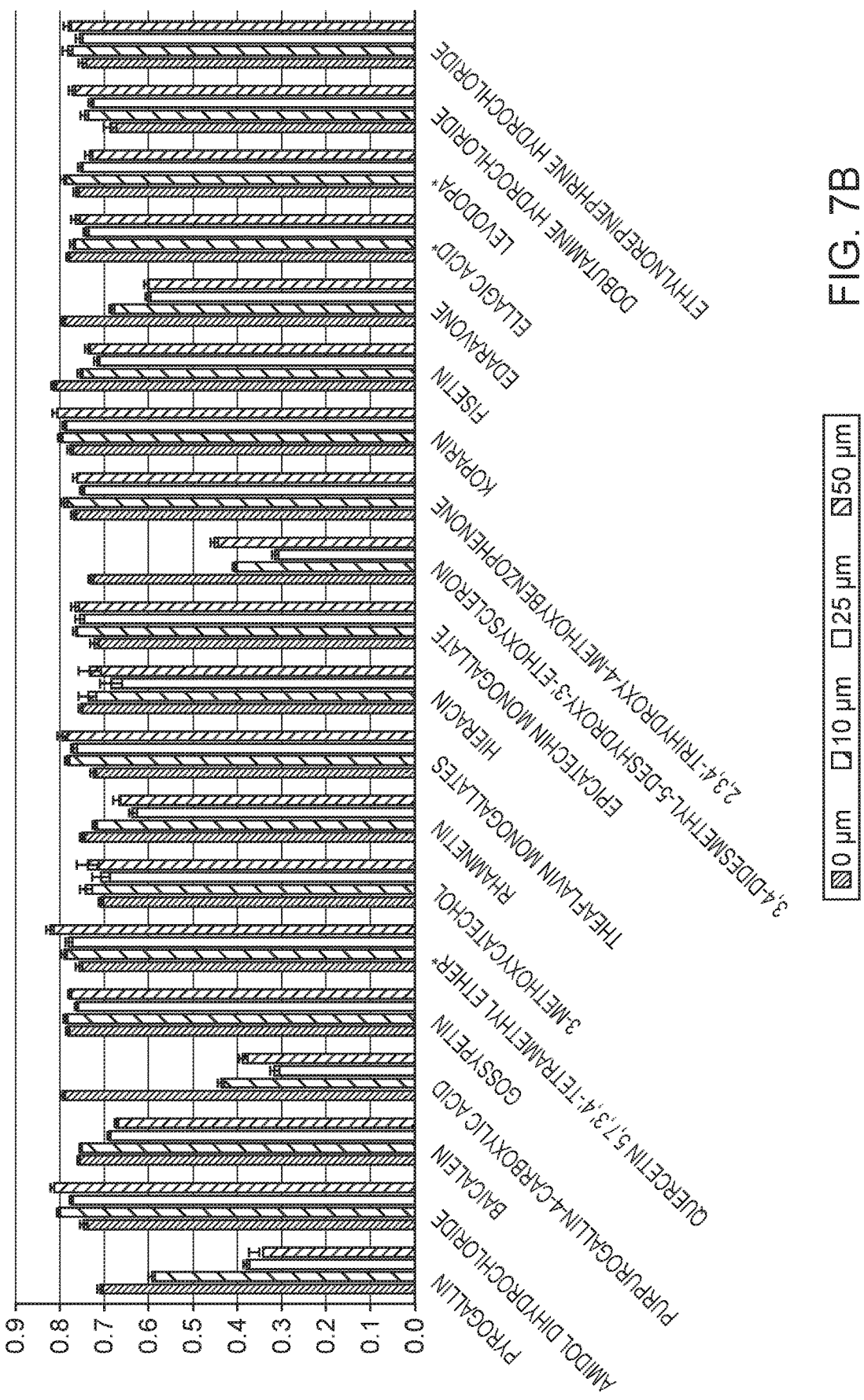
FIG. 7B illustrates a comparison of the absorbance at 600 nm of the following compounds, at concentrations of 0 μM, 10 μM, 25 μM, and 50 μM, in pSEC53-F126L/R148H (PLY66) cells: pyrogallin, amidol dihydrochloride, baicalein, purpurogallin-4-carboxylic acid, gossypetin, quercetin 5,7,3',4'-tetramethyl ether, 3-methoxycatechol, rhamnetin, theaflavin monogallates, hieracin, epicatechin monogallate, 3,4-didesmethyl-5-deshydroxy-3'-ethoxysclerion, 2,3,4'-trihydroxy-4-methoxybenzophenone, koparin, fiestin, edaravone, ellagic acid, levodopa, dobutamine hydrochloride, and ethylnorepinephrine hydrochloride.
Figure 7C:
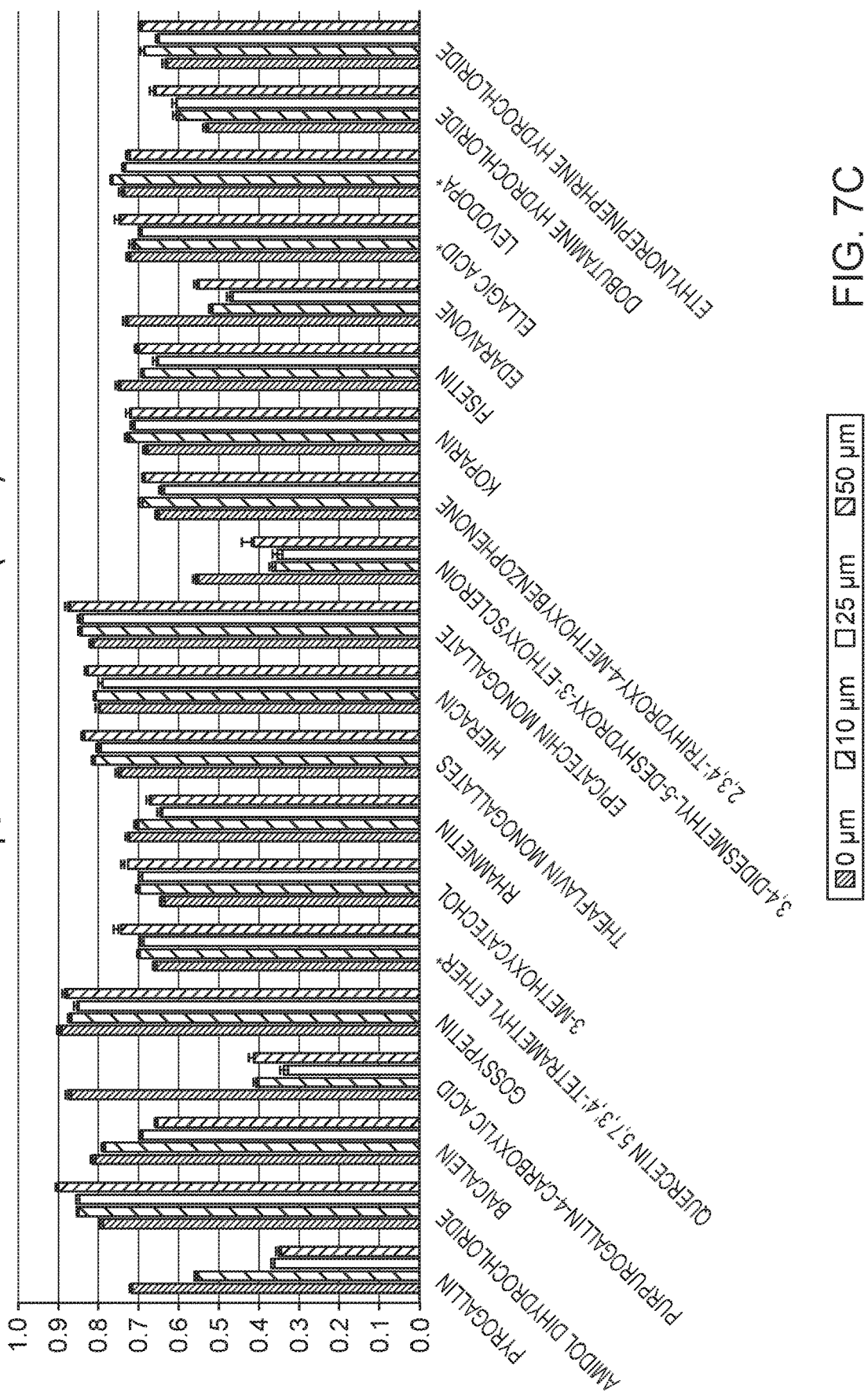
FIG. 7C illustrates a comparison of the absorbance at 600 nm of the following compounds, at concentrations of 0 μM, 10 μM, 25 μM, and 50 μM, in pSEC53-V238M/R148H (PLY67) cells: pyrogallin, amidol dihydrochloride, baicalein, purpurogallin-4-carboxylic acid, gossypetin, quercetin 5,7,3',4'-tetramethyl ether, 3-methoxycatechol, rhamnetin, theaflavin monogallates, hieracin, epicatechin monogallate, 3,4-didesmethyl-5-deshydroxy-3'-ethoxyscleroin, 2,3,4'-trihydroxy-4-methoxybenzophenone, koparin, fiestin, edaravone, ellagic acid, levodopa, dobutamine hydrochloride, and ethylnorepinephrine hydrochloride.

Similarly, suramin hexasodium (the hexasodium salt of Compound 3) also rescues growth of the pSEC53 variants more than the pACT1 variant and diploids more strongly than haploids (FIG. 1C and FIG. 2C). Growth of pSEC53-F126L improved by 24.5%, pSEC53-F126L/R148H by 47.4%, pSEC53-V238M by 16.1%, and pSEC53-V238M/R148H by 38.9%. In contrast, pACT1-F126L cells showed 6.7% improvement and pACT1-F126L/R148H showed 22.6%.

To determine whether these compounds rescue growth by increasing PMM2 enzymatic activity, human fibroblast cells (GM20942) containing the F119L/R148H heterozygous mutations and wild type fibroblast cells were treated with each compound. The cell lysates were subjected to the PMM2 enzymatic reaction. It was found that Compound 1 rescues the enzymatic activity in the F119L/R148H cells (FIG. 3-6). Based on these results, Compound 2 and the hexasodium salt of Compound 3 had no discernible effect on PMM2 enzyme activity but still caused growth rescue.

Identification of Other Compounds for PMM2

Epalrestat and rhetsinine were also tested on the above described cell models. These compounds were both found to increase PMM2 enzyme activity, and epalrestat also rescued yeast growth defect.

Example 3

A F119L point mutation strain, orthologous F125L in worms was created. The pmm-$2^{F125L/F125L}$ strains are homozygous viable and do not exhibit larval lethality, growth defects or any observable locomotor defects in liquid media. They do reach adulthood slightly slower than their heterozygous counterparts (strain name: VC3054), but not significantly enough for a compound rescue screen. This means that the F125L mutant strain is capable of behaving similarly to WT animals and do not present a screenable phenotype.

Because an underlying defect in glycosylation may be manifested when subjected to external chemical stressors, Pmm-2 F119L homozygous animals were subjected to Tunicamycin and Bortezomib drug exposures. Tunicamycin is an inhibitor of N-linked glycosylation and Bortezomib (Bzb) is an irreversible inhibitor of the proteasome. It was contemplated that either or both drugs would affect the Pmm-2 mutants differently compared to wild type ("WT"). When subjected to increasing concentrations of tunicamycin, no major differences in growth of the animals in liquid culture were seen. Whereas with Bzb, Pmm-2 mutants showed delayed growth at the highest tested concentrations of Bzb relative to wildtype animals.

Thus, Bzb-induced growth suppression was used as a means to identify compounds that might rescue the global effects of exacerbated glycosylation deficiency. Using this approach, animals were age-synchronized to obtain L1 larvae. Fifteen L1 larvae were dispensed into wells of a 384-well plate containing 25 μM of drugs (obtained from the MicroSource Spectrum library purchased from MicroSource Discovery Systems) and 11 μM Bzb. Bacterial media at fixed optical density was added to wells to enable worms to grow for a 5 day period. Animals were dispensed using Biosorter, a large particle flow cytometer by Union Biometrica, Mass. At the end of the 5 day period, animals were treated with 15 μls of 8 mM sodium azide (for 55 μls of total assay volume). After 20 minutes, immobilized animals were imaged using a plate imager under transmitted light. A custom image processing script was used to extract the areas occupied by worms/well over a 5 day period. Each plate has positive controls (no Bzb) and negative controls (11 μM Bzb) that was used to determine the z score of test wells per plate. After outlier correction for each plate in each replicate, data from all three replicates was compared. Wells per plate with positive z scores greater than 2 were identified as "hits." If hits reproduced across all three replicates were then compared. Twenty compounds were found to have positive z scores (indicating increased growth) relative to negative controls (see Table 1). At least 13 of the 20 compounds belong to the category of antioxidants; still others fall in the category of catecholamines

TABLE 1

| Compound Name | Replicate ("rep") Number | Area (Au) | Z-score relative to Negative Controls (Au) | Status |
|---|---|---|---|---|
| PYROGALLIN | rep4 | 250634 | 7.10154 | HIT |
| PYROGALLIN | rep2 | 446410 | 9.22022 | HIT |
| PYROGALLIN | rep1 | 363173 | 3.50207 | HIT |
| AMIDOL DIHYDROCHLORIDE | rep4 | 213872 | 5.42515 | HIT |
| AMIDOL DIHYDROCHLORIDE | rep2 | 391001 | 6.86149 | HIT |
| AMIDOL DIHYDROCHLORIDE | rep1 | 365518 | 3.55825 | HIT |
| BAICALEIN | rep4 | 166745 | 3.27609 | HIT |
| BAICALEIN | rep2 | 383090 | 6.52472 | HIT |
| BAICALEIN | rep1 | 318707 | 2.43674 | HIT |
| PURPUROGALLIN-4-CARBOXYLIC ACID | rep4 | 156513 | 2.8095 | HIT |
| PURPUROGALLIN-4-CARBOXYLIC ACID | rep2 | 313325 | 3.55486 | HIT |
| PURPUROGALLIN-4-CARBOXYLIC ACID | rep1 | 304572 | 2.09809 | HIT |
| GOSSYPETIN | rep4 | 210243 | 5.25966 | HIT |
| GOSSYPETIN | rep2 | 358709 | 5.48683 | HIT |
| GOSSYPETIN | rep1 | 355885 | 3.32746 | HIT |
| QUERCETIN 5,7,3,4'-TETRAMETHYL ETHER | rep4 | 200078 | 4.79612 | HIT |
| QUERCETIN 5,7,3,4'-TETRAMETHYL ETHER | rep2 | 431061 | 8.56682 | HIT |
| QUERCETIN 5,7,3,4'-TETRAMETHYL ETHER | rep1 | 433217 | 5.1802 | HIT |
| 3-METHOXYCATECHOL | rep4 | 170467 | 6.94283 | HIT |
| 3-METHOXYCATECHOL | rep2 | 438404 | 9.16124 | HIT |
| 3-METHOXYCATECHOL | rep1 | 375691 | 4.53797 | HIT |
| RHAMNETIN | rep4 | 181260 | 7.63799 | HIT |
| RHAMNETIN | rep2 | 517284 | 12.6009 | HIT |
| RHAMNETIN | rep1 | 296671 | 2.34381 | HIT |
| THEAFLAVIN MONOGALLATES | rep4 | 165849 | 6.64539 | HIT |
| THEAFLAVIN MONOGALLATES | rep2 | 394357 | 7.24051 | HIT |
| THEAFLAVIN MONOGALLATES | rep1 | 322783 | 3.06887 | HIT |
| HIERACIN | rep4 | 139118 | 4.9237 | HIT |
| HIERACIN | rep2 | 390470 | 7.07101 | HIT |
| HIERACIN | rep1 | 381046 | 4.68667 | HIT |
| EPICATECHIN MONOGALLATE | rep4 | 108617 | 2.95918 | HIT |
| EPICATECHIN MONOGALLATE | rep2 | 286182 | 2.52339 | HIT |
| EPICATECHIN MONOGALLATE | rep1 | 411579 | 5.53448 | HIT |
| 3,4-DIDESMETHYL-5-DESHYDROXY-3'-ETHOXYSCLEROIN | rep4 | 223545 | 10.3615 | HIT |

TABLE 1-continued

| Compound Name | Replicate ("rep") Number | Area (Au) | Z-score relative to Negative Controls (Au) | Status |
|---|---|---|---|---|
| 3,4-DIDESMETHYL-5-DESHYDROXY-3'-ETHOXYSCLEROIN | rep2 | 302280 | 3.22537 | HIT |
| 3,4-DIDESMETHYL-5-DESHYDROXY-3'-ETHOXYSCLEROIN | rep1 | 296599 | 2.34181 | HIT |
| 2,3,4'-TRIHYDROXY-4-METHOXY-BENZOPHENONE | rep4 | 172895 | 7.09921 | HIT |
| 2,3,4'-TRIHYDROXY-4-METHOXY-BENZOPHENONE | rep2 | 423682 | 8.51926 | HIT |
| 2,3,4'-TRIHYDROXY-4-METHOXY-BENZOPHENONE | rep1 | 294576 | 2.28564 | HIT |
| KOPARIN | rep4 | 191377 | 8.2896 | HIT |
| KOPARIN | rep2 | 285710 | 2.50281 | HIT |
| KOPARIN | rep1 | 322013 | 3.04749 | HIT |
| FISETIN | rep4 | 176726 | 4.11602 | HIT |
| FISETIN | rep2 | 363708 | 5.11805 | HIT |
| FISETIN | rep1 | 313681 | 2.50695 | HIT |
| EDARAVONE | rep4 | 172084 | 4.20843 | HIT |
| EDARAVONE | rep2 | 384198 | 10.0789 | HIT |
| EDARAVONE | rep1 | 311245 | 4.19514 | HIT |
| ELLAGIC ACID | rep4 | 217398 | 6.47839 | HIT |
| ELLAGIC ACID | rep2 | 461290 | 12.7164 | HIT |
| ELLAGIC ACID | rep1 | 231110 | 2.28306 | HIT |
| LEVODOPA | rep4 | 165461 | 3.2216 | HIT |
| LEVODOPA | rep2 | 397572 | 5.59083 | HIT |
| LEVODOPA | rep1 | 311801 | 2.3866 | HIT |
| DOBUTAMINE HYDROCHLORIDE | rep4 | 190942 | 4.68037 | HIT |
| DOBUTAMINE HYDROCHLORIDE | rep2 | 274396 | 2.65442 | HIT |
| DOBUTAMINE HYDROCHLORIDE | rep1 | 407938 | 4.87083 | HIT |
| ETHYLNOREPINEPHRINE HYDROCHLORIDE | rep4 | 173137 | 3.76743 | HIT |
| ETHYLNOREPINEPHRINE HYDROCHLORIDE | rep2 | 416364 | 7.80611 | HIT |
| ETHYLNOREPINEPHRINE HYDROCHLORIDE | rep1 | 413271 | 5.00298 | HIT |

Hits found to have activity in all replicates of the Pmm-2 nematode screen were tested in yeast PMM2 models (as described above). The yeast PMM2 growth assay does not use Bzb in assay conditions. Several compounds rescued the growth defect in PMM2 diploid yeast models indicating that rescue may occur through a conserved mechanism of action unique to PMM2 pathophysiology.

Unless otherwise defined, all technical and scientific terms used herein have the same meaning as commonly understood by one of ordinary skill in the art to which this invention belongs.

The inventions illustratively described herein may suitably be practiced in the absence of any element or elements, limitation or limitations, not specifically disclosed herein. Thus, for example, the terms "comprising", "including," "containing", etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed.

All publications, patent applications, patents, and other references mentioned herein are expressly incorporated by reference in their entirety, to the same extent as if each were incorporated by reference individually. In case of conflict, the present specification, including definitions, will control.

It is to be understood that while the disclosure has been described in conjunction with the above embodiments, that the foregoing description and examples are intended to illustrate and not limit the scope of the disclosure. Other aspects, advantages and modifications within the scope of the disclosure will be apparent to those skilled in the art to which the disclosure pertains.

The invention claimed is:

1. A method for treating a congenital disorder of glycosylation in a patient in need thereof comprising administering a therapeutically effective amount of an aldose reductase inhibitor, wherein the aldose reductase inhibitor is a compound, or a pharmaceutically acceptable salt thereof, selected from: α-cyano-4-hydroxycinnamic acid, epalrestat, and rhetsinine and wherein the congenital disorder of glycosylation is a N-linked glycosylation disorder.

2. A method for treating phosphomannomutase deficiency in a patient in need thereof comprising administering a therapeutically effective amount of an aldose reductase inhibitor, wherein the aldose reductase inhibitor is a compound, or a pharmaceutically acceptable salt thereof, selected from: α-cyano-4-hydroxycinnamic acid, epalrestat, and rhetsinine.

3. The method of claim 1, wherein the aldose reductase inhibitor is epalrestat.

4. The method of claim 1, wherein the patient is further administered a therapeutically effective amount of another therapeutic agent, wherein the another therapeutic agent is an aldose reductase inhibitor.

5. The method of claim 4, wherein the another therapeutic agent is.

6. The method of claim 2, wherein the aldose reductase inhibitor is epalrestat.

7. The method of claim 2, wherein the patient is further administered a therapeutically effective amount of another therapeutic agent, wherein the another therapeutic agent is an aldose reductase inhibitor.

8. The method of claim 1, wherein the aldose reductase inhibitor is administered as a pharmaceutical composition.

9. The method of claim 2, wherein the aldose reductase inhibitor is administered as a pharmaceutical composition.

10. The method of claim 8, wherein the pharmaceutical composition is formulated to provide a sustained or delayed release of the aldose reductase inhibitor.

11. The method of claim 9, wherein the pharmaceutical composition is formulated to provide a sustained or delayed release of the aldose reductase inhibitor.

12. The method of claim 1, wherein the aldose reductase inhibitor is administered once, twice, or three times daily.

13. The method of claim 2, wherein the aldose reductase inhibitor is administered once, twice, or three times daily.

* * * * *